US012201338B2

(12) United States Patent
Bowen et al.

(10) Patent No.: US 12,201,338 B2
(45) Date of Patent: Jan. 21, 2025

(54) ARTICULATING TOOL FOR ENDOSCOPIC PLACEMENT OF FASTENERS

(71) Applicant: Pro-Dex, Inc., Irvine, CA (US)

(72) Inventors: Joshua Bowen, Irvine, CA (US); Mark Fanous, Irvine, CA (US); Jake Huntley, Irvine (CA)

(73) Assignee: Pro-Dex, Inc., Irvine, CA (US)

( * ) Notice: Subject to any disclaimer, the term of this patent is extended or adjusted under 35 U.S.C. 154(b) by 141 days.

(21) Appl. No.: 17/650,362

(22) Filed: Feb. 8, 2022

(65) Prior Publication Data

US 2022/0338914 A1 Oct. 27, 2022

Related U.S. Application Data

(63) Continuation of application No. 16/783,596, filed on Feb. 6, 2020, now Pat. No. 11,259,855, which is a continuation of application No. PCT/US2018/045851, filed on Aug. 8, 2018.

(60) Provisional application No. 62/590,122, filed on Nov. 22, 2017, provisional application No. 62/567,584, filed on Oct. 3, 2017, provisional application No. 62/543,551, filed on Aug. 10, 2017.

(51) Int. Cl.
*A61B 17/88* (2006.01)
*A61B 17/00* (2006.01)
*A61B 17/80* (2006.01)

(52) U.S. Cl.
CPC .... *A61B 17/8875* (2013.01); *A61B 17/00234* (2013.01); *A61B 17/808* (2013.01); *A61B 2017/00238* (2013.01)

(58) Field of Classification Search
CPC .......... A61B 17/8875; A61B 17/00234; A61B 17/808; A61B 2017/00238
See application file for complete search history.

(56) References Cited

U.S. PATENT DOCUMENTS

| 4,662,814 A | 5/1987 | Suzuki et al. |
| 5,484,440 A | 1/1996 | Allard |
| 5,660,491 A | 8/1997 | Roberts et al. |
| 6,658,962 B1 | 12/2003 | Rosheim |
| 9,140,344 B2 | 9/2015 | Teng et al. |
| 9,265,551 B2 | 2/2016 | Kust et al. |
| 9,421,003 B2 | 8/2016 | Williams et al. |

(Continued)

FOREIGN PATENT DOCUMENTS

| EP | 2364825 A1 | 9/2011 |
| JP | 2014-155826 A | 8/2014 |

(Continued)

OTHER PUBLICATIONS

Office Action in corresponding Japanese Patent Application No. 2020-506780, dated Aug. 9, 2022, in 17 pages.

(Continued)

*Primary Examiner* — Sameh R Boles
(74) *Attorney, Agent, or Firm* — Knobbe, Martens, Olson & Bear, LLP

(57) ABSTRACT

Various articulating tools for endoscopic placement of fasteners are disclosed. The tool can comprise a multi-angle articulating screwdriver. The tool can have an elongate shaft with an articulating driver head at a distal end. The tool can rotate the articulating driver head to drive fasteners, such as screws, to a surgical site. The articulating driver head can articulate with respect to a longitudinal axis of the elongate shaft to enable the fastener to be driven at various angle. The tool can be coupled to a powered handpiece power and can transmit torque from the handpiece to the driver head.

10 Claims, 26 Drawing Sheets

(56) References Cited

U.S. PATENT DOCUMENTS

| | | |
|---|---|---|
| 11,259,855 B2 | 3/2022 | Bowen et al. |
| 2002/0183762 A1 | 12/2002 | Anderson et al. |
| 2009/0023988 A1 | 1/2009 | Komer et al. |
| 2011/0152867 A1 | 6/2011 | Petrzelka et al. |
| 2011/0301416 A1 | 12/2011 | Dejima et al. |
| 2012/0266709 A1* | 10/2012 | Wang ................. B25F 3/00 74/417 |
| 2012/0271285 A1 | 10/2012 | Sholev et al. |
| 2014/0236174 A1 | 8/2014 | Williams et al. |
| 2016/0106442 A1 | 4/2016 | Guo et al. |
| 2017/0281171 A1* | 10/2017 | Shelton, IV ....... A61B 17/1155 |
| 2018/0021960 A1 | 1/2018 | Grant et al. |
| 2023/0414264 A1 | 12/2023 | Taber et al. |

FOREIGN PATENT DOCUMENTS

| | | |
|---|---|---|
| WO | WO 2011/019206 A2 | 2/2011 |
| WO | WO 2011/092692 A2 | 8/2011 |
| WO | WO 2019/032729 A1 | 2/2019 |

OTHER PUBLICATIONS

International Search Report and Written Opinion in corresponding international Patent Application No. PCT/US2018/045851, dated Oct. 19, 2018, in 9 pages.

International Preliminary Report on Patentability in corresponding international Patent Application No. PCT/US2018/045851, dated Feb. 20, 2020, in 7 pages.

Extended Search Report in corresponding European Patent Application No. 18844527.4, dated Aug. 2, 2021, in 12 pages.

Office Action in corresponding New Zealand Patent Application No. 761369, dated Nov. 15, 2021, 2021, in 3 pages.

Petrzelka et al., "An Articulating Tool for Endoscopic Screw Delivery," Proceedings of the 2010 Design of Medical Devices Conference, Apr. 13-15, 2010, in 8 pages.

Office Action in corresponding Australian Patent Application No. 2018313842, dated Jul. 24, 2023, in 4 pages.

* cited by examiner

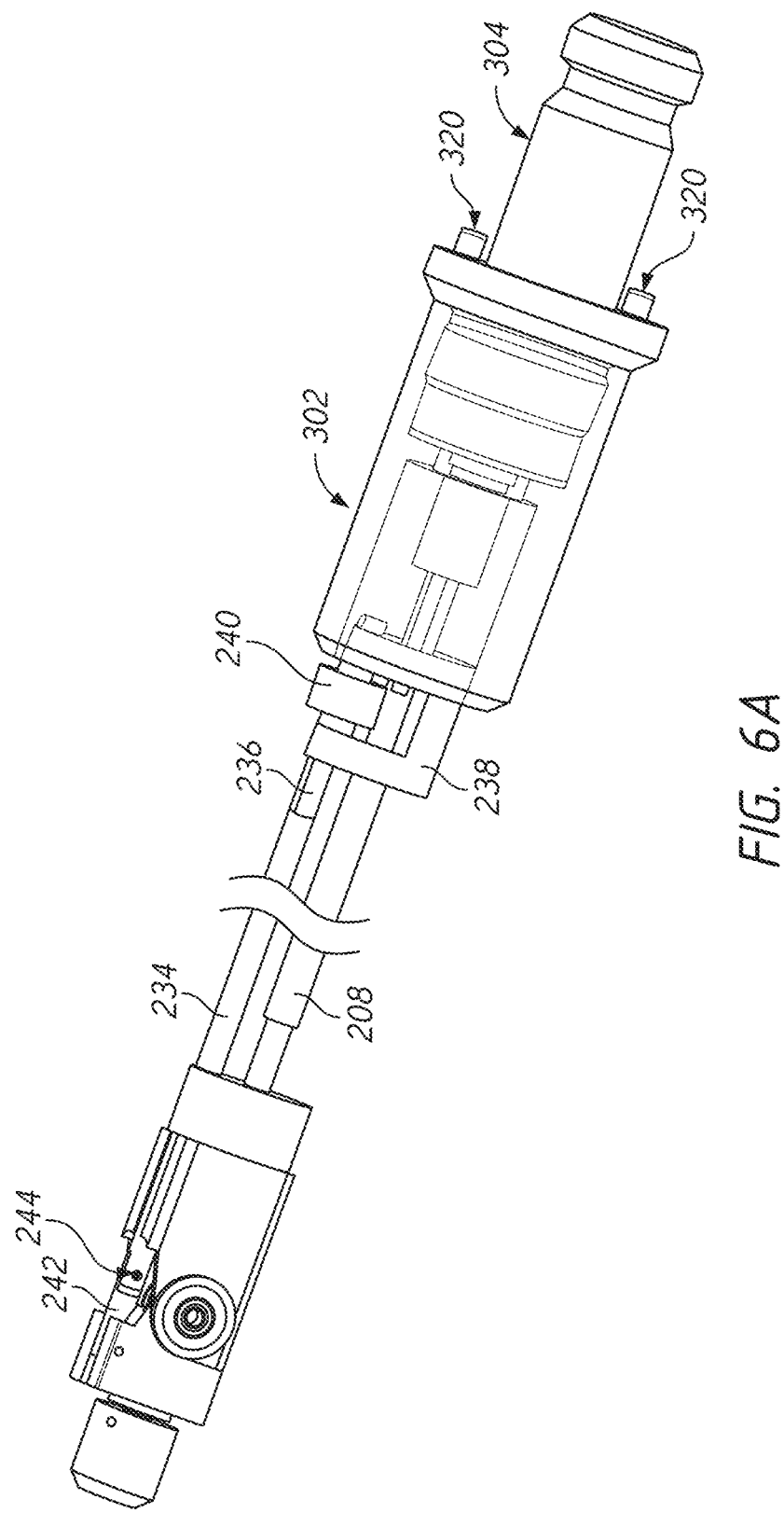

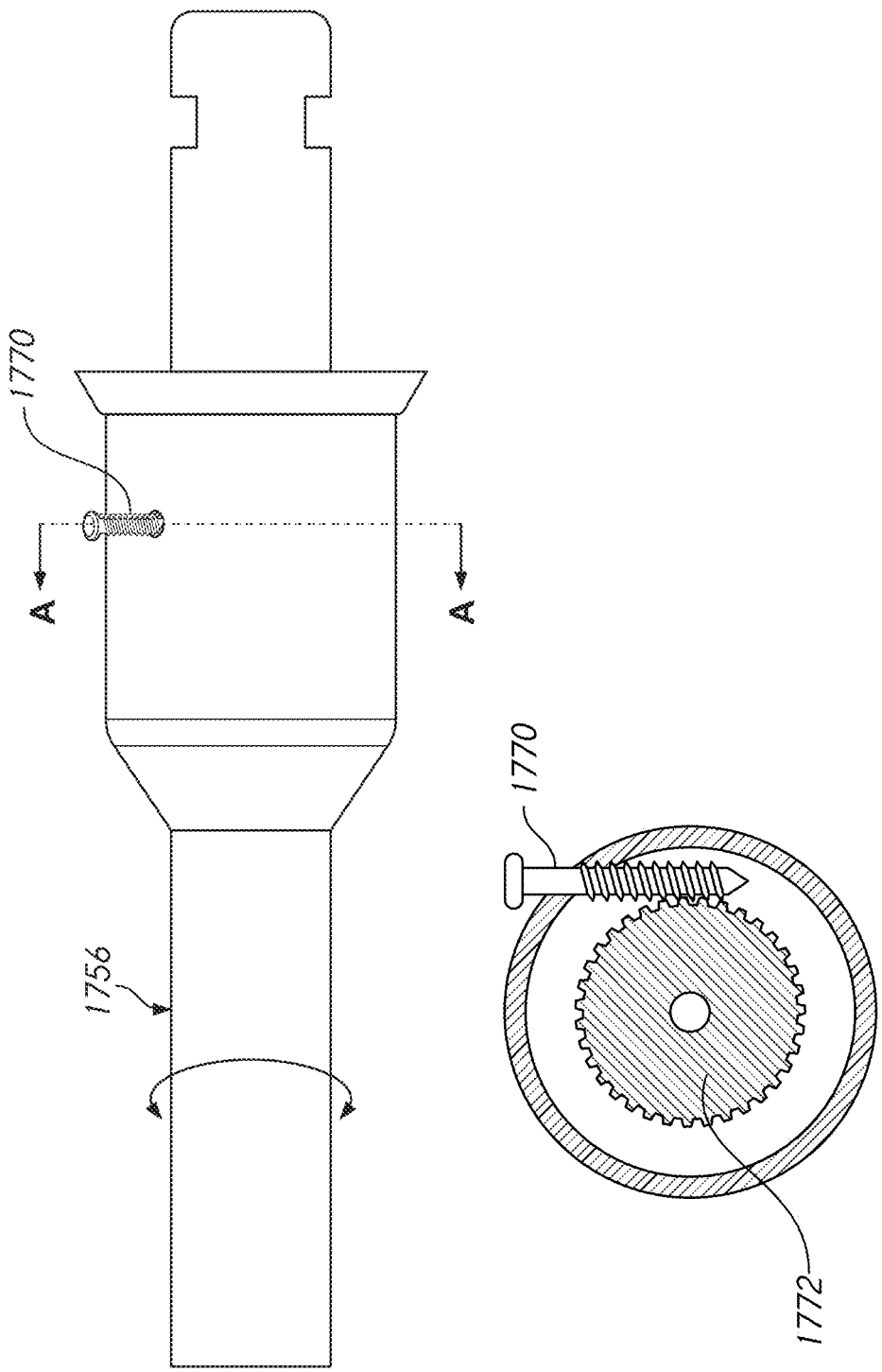

ARTICULATING TOOL FOR ENDOSCOPIC PLACEMENT OF FASTENERS

CROSS-REFERENCE

This application is a continuation of U.S. application Ser. No. 16/783,596, filed Feb. 6, 2020, now U.S. Pat. No. 11,259,855, which claims the benefit under 35 U.S.C. § 120 and 35 U.S.C. § 365 (c) as a continuation of International Application No. PCT/US2018/045851, designating the United States, with an international filing date of Aug. 8, 2018, titled "ARTICULATING TOOL FOR ENDOSCOPIC PLACEMENT OF FASTENERS," which claims the benefit of U.S. Patent Application No. 62/543,551, filed Aug. 10, 2017; U.S. Patent Application No. 62/567,584, filed Oct. 3, 2017; and U.S. Patent Application No. 62/590,122, filed Nov. 22, 2017. The entirety of each of the aforementioned applications is incorporated by reference herein.

BACKGROUND

Field

This disclosure relates to an articulating tool for endoscopic placement of fasteners, such as screws.

Certain Related Art

Various surgical procedures (such as bone fracture surgeries) include inserting one or more screws into a bone to retain a structure, such as a plate (e.g., titanium osteosynthetic plates or others) on the bone. During insertion, the screw is threaded into the bone. For example, to treat a rib fracture, a surgeon can attach a plate with one or more fixation screws to an inner surface (on the side facing the lungs) of the broken rib. The surgery can be performed in a minimally invasive manner with the aid of a thoracoscope. The view from the thoracoscope can allow visualization of the inner side of the rib cage, including the fracture site(s). Thoracoscope-assisted internal fixation of fractured ribs can be more beneficial to a patient than certain other treatments, such as analgesia and/or ventilation.

SUMMARY OF CERTAIN FEATURES

Inserting screws into a bone can be challenging due to the location and/or orientation of the bone, the surrounding anatomical structures (for example, muscles, ligaments, tendons, blood vessel, nerves, or otherwise), and/or the shape of the bone. In certain surgical procedures, there can be limited access to a desired insertion location and/or angle for the screw on the bone. Retracting the fastening tool to adjust the insertion location and/or angle may be time consuming, cause trauma to the patient, and/or be inconvenient or impractical (such as when a direct entry path for the fastening tool is blocked by other anatomical structures).

An extension with flexible or elastomeric portions may aid in navigating a driver head in the patient's body. However, the flexible or elastomeric portions may not efficiently transmit a torque sufficient for inserting a screw into the cortex of the bone.

A rigid and/or non-flexible and non-elastomeric fastening tool that can change direction may aid in navigating a driver head in the patient's body while also efficiently transmitting a torque. In some embodiments, such an extension (e.g., a screwdriver) can include an articulating component that is configured to articulate at multiple angles in multiple axes. This can allow the fastening tool to adjust (e.g., bend or pivot) so as to access tight spaces, reduce a frequency of a user readjusting the position, and/or provide a desired orientation of the fastening tool. It can be beneficial that the fastening tool can at the same time maintain sufficient torque outputs to perform the intended function (e.g., to insert a fixation screw into the bone).

It can be beneficial to have an extension with an articulating component that has an outer profile comparable to a standard non-articulating fastening tool. A smaller outer profile can reduce the need for a larger-sized access portal (e.g., a trocar) and/or allow the fastening tool with the articulating component to access spaces that are usually accessible by the standard non-articulating fastening tool.

In some implementations, gearing (e.g., bevel or miter gears) can provide improved overall range for the articulating component, such as an articulating driver head. It can be desirable to use gears and gearing mechanisms that will fit into the available space while maintaining sufficient torque outputs to perform the original function.

Several embodiments of an articulating tool for endoscopic placement of fasteners are disclosed herein that provide one or more of the above-described benefits, or other benefits.

Any of the structures, materials, steps, or other features disclosed above, or disclosed elsewhere herein, can be used in any of the embodiments in this disclosure. Any structure, material, step, or other feature of any embodiment can be combined with any structure, material, step, or other feature of any other embodiment to form further embodiments, which are part of this disclosure.

The preceding summary, following detailed description, and associated drawings do not limit or define the scope of protection. The scope of protection is defined by the claims.

BRIEF DESCRIPTION OF THE DRAWINGS

The abovementioned and other features of the embodiments disclosed herein are described below with reference to the drawings of the embodiments. The illustrated embodiments are intended to illustrate, but not to limit the embodiments. Various features of the different disclosed embodiments can be combined to form further embodiments, which are part of this disclosure.

FIG. 6A illustrates a perspective view of the fastening tool of FIG. 2, with the outer housing not shown and a collet housing shown as transparent for illustration purposes.

FIG. 17 illustrates a shaft rotating mechanism configured for rotating the driver head.

DETAILED DESCRIPTION OF CERTAIN EMBODIMENTS

A variety of articulating tools are described below to illustrate various examples that may be employed to achieve one or more desired improvements. These examples are illustrative only and not intended to restrict the general inventions presented and the various aspects and features of these inventions. The phraseology and terminology used herein is for the purpose of description and should not be regarded as limiting. No features, structure, or step disclosed herein is essential or indispensable.

Overview

Figures 1A, 1B:
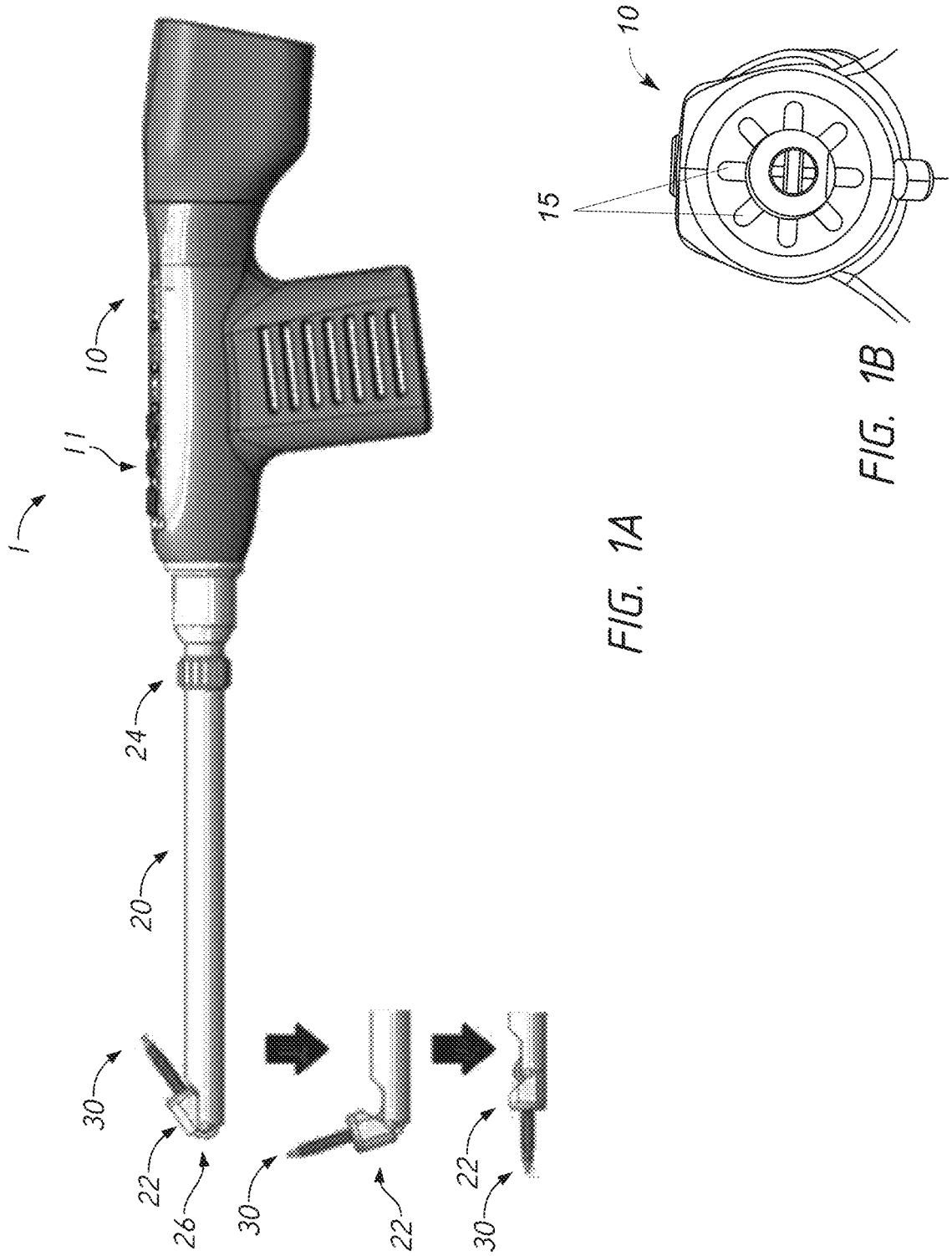
FIG. 1A illustrates a side view of an example fastening tool coupled to a handpiece and an articulating driver head shown at different angles.
FIG. 1B illustrates a front view of an example fastening tool interface of the handpiece.

In several embodiments, an articulating tool 1 is configured to facilitate endoscopic placement of fasteners. For example, the articulating tool 1 may be used to drive screws into bone during a surgical procedure. As shown in FIG. 1A, the articulating tool 1 can include a handpiece 10 and a fastening tool 20. The handpiece 10 can be a powered device, such as having a battery and electric motor. The handpiece 10 can include a grip for a user to grasp and manipulate the articulating tool 1. The handpiece 10 can include controls (e.g., buttons) to operate the articulating tool 1, such as to direct driving action, speed, and/or direction (e.g., clockwise or counter clockwise). The fastening tool 20 can be coupled to the handpiece 10, such as at a proximal end of the fastening tool 20. The fastening tool 20 can be removably connected to the handpiece 10. In certain embodiments, the fastening tool 20 is coupled to the handpiece 10 with a quick-release mechanism. In some embodiments, the quick-release mechanism comprises a release button or lever on the fastening tool 20 or the handpiece 10 so that actuating (e.g., depressing) the button or lever can release the attachment of the fastening tool 20 to the handpiece 10.

The fastening tool 20 can include an articulating driver head adapter 22 at a distal end of the fastening tool 20. The adapter 22 can couple to a driver head 30 (e.g., a bit configured to engage with the head of a screw). For example, the adapter 22 can couple to the driver head 30 releasably and/or via a quick-release mechanism, such as a detent.

In several embodiments, the adapter 22 is configured to rotate. As illustrated, the adapter 22 can be configured to rotate about a joint 26 and relative to a longitudinal axis L of the fastening tool 20. Rotation of the adapter 22 can enable the position and angle of the adapter 22 (and thus the driver head 30) to be adjusted, which can facilitate driving of a fastener at a desired position and angle. In some embodiments, the adapter 22 is rotatable in one plane and/or about an axis of rotation that is generally perpendicular to the longitudinal axis L. In certain embodiments, the adapter 22 can rotate approximately 0° to approximately 140° (such as shown in FIG. 1A), or approximately 0° to approximately 110°, or approximately 0° to approximately 90°, or approximately 0° to approximately 45°. The fastening tool 20 can include an articulation actuator configured to adjust the angle of the adapter 22. In the example shown in FIG. 1A, the articulation actuator comprises an adjustment dial 24, such as a manually operated wheel. The actuator can be located away from the driver head adapter 22, such as at or near the proximal end of the fastening tool 20.

The handpiece 10 or the fastening tool 20 can include a driver head actuator, such as a button, thumbwheel, lever, or otherwise. For example, the handpiece 10 can include one or more buttons 11 that operates the motor, which can be operatively connected to the driver head 30, such as to rotate the drive head 30 (e.g., clockwise and/or counterclockwise). In some embodiments, power from the motor is transmitted to the driver head 30 through an internal shaft of the fastening tool 20 and/or through the joint 26. In some embodiments, the handpiece 10 can include software and/or hardware for adaptively limiting torque applied to the driver head 30. Additional information about adaptive torque limiting can be found in U.S. Pat. No. 9,265,551, the entirety of which is incorporated by reference herein.

In some embodiments, such as shown in FIG. 1B, the fastening tool 20 can be indexed to the handpiece 10 in a variety of orientations. For example, the fastening tool 20 can be secured to the handpiece 10 in a plurality (e.g., 2, 3, 4, 6, 8, or more) of rotational positions, such as with mating features 15 (e.g., recesses and protrusions) in the handpiece 10 and fastening tool 20. Rotating the fastening tool 20 to a new orientation relative to the handpiece 10 can rotate the driver head 30 to a new orientation as well. This can enable the drive head 30 to drive fasteners in a variety of orientations relative to the handpiece 10. In some implementations, by rotating the driver head 30, which can be configured to articulate in one plane, through the different orientations of the fastening tool 20, the articulating tool 1 can be configured to articulate in those different planes (such as being able to articulate in a half sphere of space in which the driver head 30 can be operated in). In various embodiments, the fastening tool 20 can be detached from the handpiece 10, rotated relative to the handpiece 10 to a new position, then reattached to the handpiece to allow for a new range of operation of the driver head 30.

Certain Embodiments of an Articulating Fastening Tool

Figure 2:
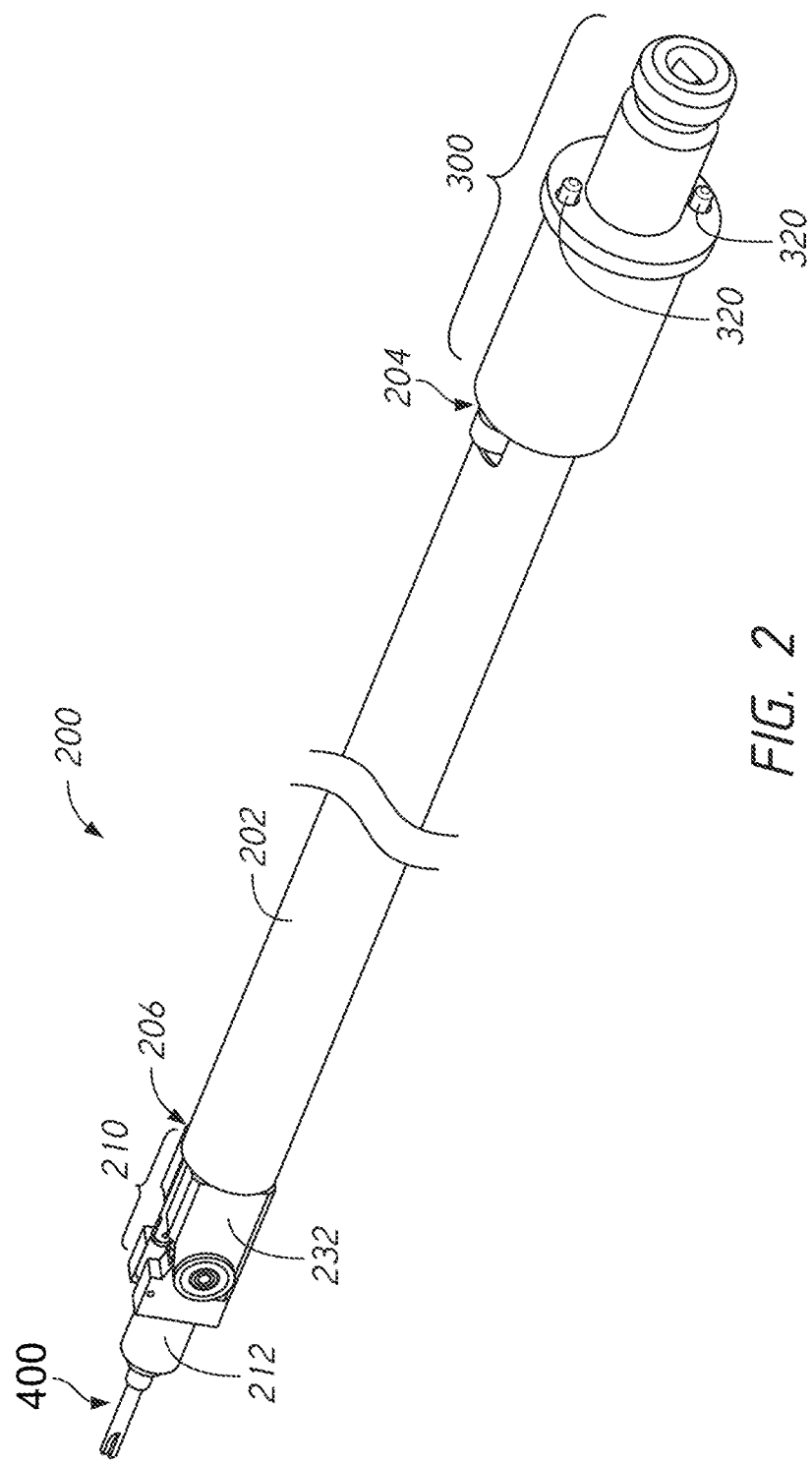
FIG. 2 illustrates a perspective view of an example fastening tool with an articulating driver head at about 0° with respect to a longitudinal axis of the fastening tool.

Various embodiments of an articulating fastening tool 200 are disclosed. As shown in FIG. 2, the fastening tool 200 can have any of the features of the fastening tool 20 in FIG. 1A. For example, the tool 200 can be configured to couple to a body at a proximal end of the fastening tool 200 and to a driver head 300 at the distal end of the fastening tool 200.

Figure 3A:
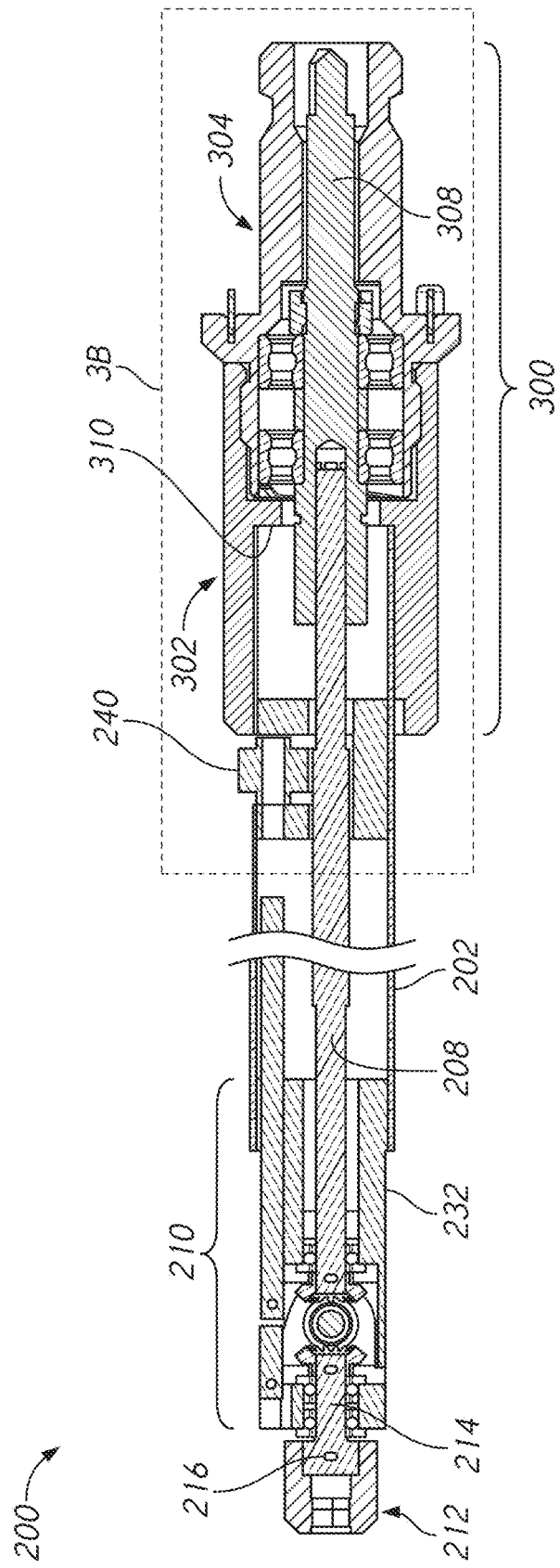
FIG. 3A illustrates a longitudinal cross-sectional view of the fastening tool of FIG. 2.
Figure 3B:
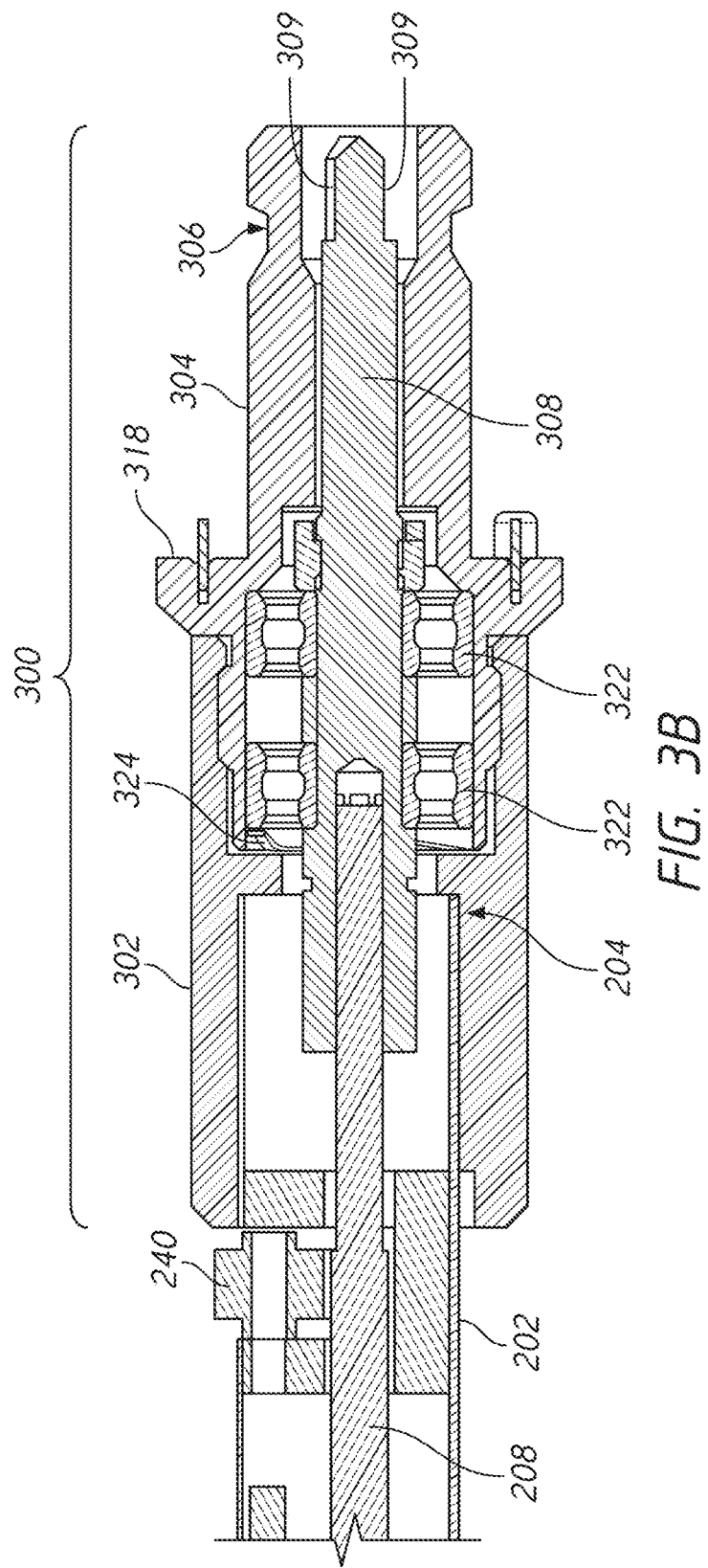
FIG. 3B illustrates a detailed cross-sectional view of a proximal portion of the fastening tool of FIG. 3A.

The fastening tool 200 can include an elongate outer housing 202 having a proximal portion 204 and a distal portion 206. A body coupling assembly 300 can be located at a proximal end of the tool 200. The body coupling assembly 300 can include a collet housing 302 coupled to the proximal portion 204 of the elongate outer housing 202. As shown in FIGS. 3A and 3B, a terminal part of the proximal portion 204 of the outer housing 202 can be received within a first cavity of the collet housing 302 and can terminate at or near a transverse wall 310. The transverse wall 310 can include a generally central opening configured to allow a collet shaft 308 to pass through and freely rotate with respect to the opening of the wall 310. In certain embodiments, the housing 202 can be rotated relative to the handpiece 10 while connected to the handpiece 10.

The collet housing 302 can include a second cavity on an opposite side of the transverse wall 310 from the first cavity. The second cavity can house a body interface 304 that extends proximally from the collet housing 302. The collet housing 302 can be received in an opening in the handpiece 10. This can functionally connect the tool 200 and the handpiece 10, such as to allow the motor of the handpiece 10 to drive the driver head 300.

Figure 3C:
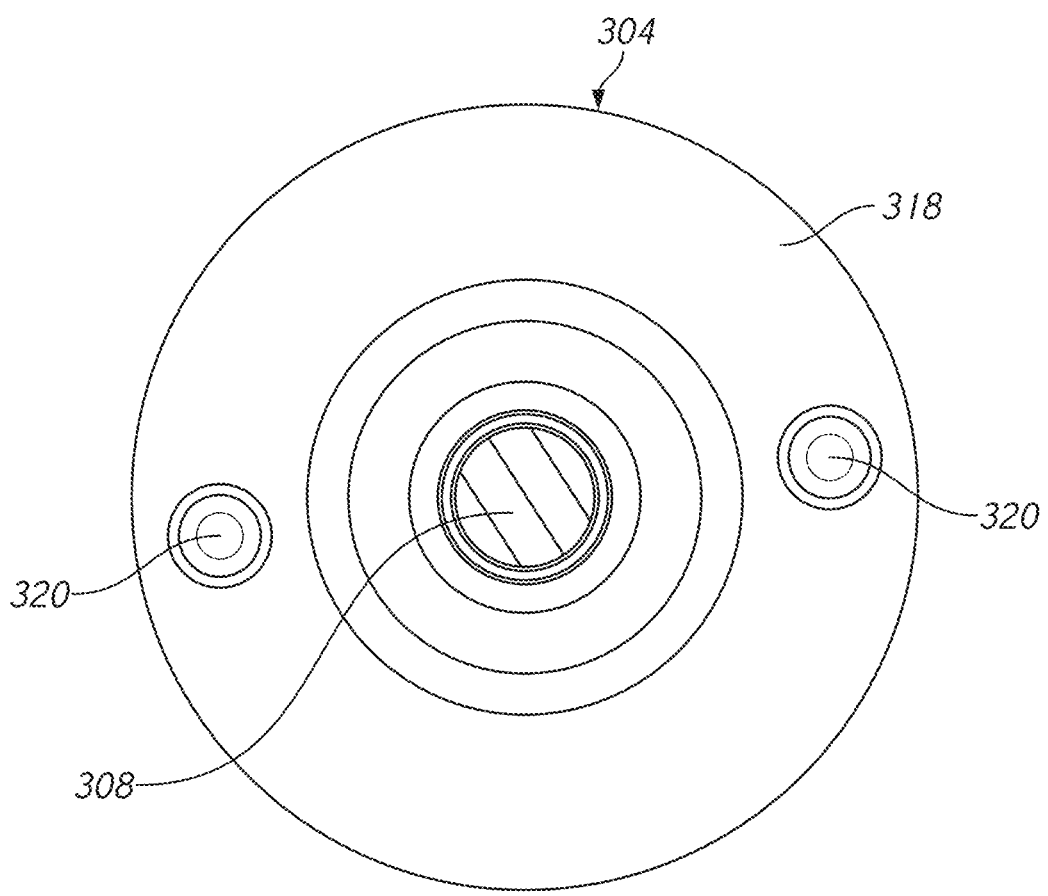
FIG. 3C illustrates a side elevation view of a proximal end of the fastening tool of FIG. 3A.

As shown in FIGS. 3A-3C, the body interface 304 can include a proximally facing surface 318. A perimeter of the proximally facing surface 318 extends radially outward from an outer surface of the collet housing 302. The proximally facing surface 318 can act as a stopper for the body, such as the handpiece 10, when installing the fastening tool 200 onto the body. One or more (for example, two, three, or more) orientation features, such as dowel pins 320, can extend proximally from the proximally facing surface 318. The dowel pins 330 can facilitate aligning the handpiece 10 with the body coupling assembly 300. The body interface 304 can include an outer groove 306 near a proximal end of the interface 304. In some embodiments, the outer groove 306 can be configured to facilitate in retaining the body.

As shown in FIGS. 3A-3C, the body interface 304 can have a lumen that is continuous from the lumens of the collet housing 302 and the elongate outer housing 202 and configured to accommodate the collet shaft 308. A proximal end of the collet shaft 308 can terminate inside the lumen of the body interface 304, which can protect the proximal end of the collet shaft 308 from external impacts. At least one (e.g., two, three, or more) ball bearings 322 can extend between an outer wall of the collet shaft 308 and a lumen wall of the body interface 304 to facilitate rotation of the collet shaft 308 in the lumen of the body interface 304 (e.g., by aiding in aligning an axis of rotation of the collet shaft 308 with a longitudinal axis of the lumen of the body interface 304). A biasing member, such as a wave washer 324, can be disposed between the transverse wall 310 and a distal ball bearing 322 (e.g., to inhibit or prevent the transverse wall 310 from impinging on the distal ball bearing 322).

The proximal end of the collet shaft 308 can be configured to couple with a handpiece drive shaft, which can be operably coupled to the motor. The collet shaft 308 can include a rotation-limiting shape, such as at least one flat surface. In some embodiments, such as shown in FIGS. 3A and 3B, the rotation limiting shape can include two opposing flat surfaces 309. When the collet shaft 308 engages the drive shaft, rotation of the drive shaft causes rotation of the collet shaft 308.

A distal end of the collet shaft 308 can be coupled to a first shaft 208. As shown in FIGS. 3A and 3B, the distal end of the collet shaft 308 can include a recess configured to fixedly (e.g., via friction, adhesives, or otherwise) receive the first shaft 208. In some embodiments, the collet shaft 308 and the first shaft 208 can be fixedly engaged by other attachment features and/or mechanisms. As will be described below, the first shaft 208 is configured to transmit a rotation of the collet shaft 308 and/or torque to the driver head, such as the driver head 300.

The first shaft 208 can be positioned inside and/or extend through the lumen of the elongate outer housing 202. A distal portion of the first shaft 208 can extend distally from the elongate outer housing 202 and into an articulating torque transmission unit 210, such as a bevel gear assembly. The articulation unit can be located distally from the elongate outer housing 202. The articulating torque transmission unit 210 can include an output shaft 214 fixedly coupled to a driver head adapter 212 (e.g., via a press fit pin 216 extending through a pin hole in a distal portion of the output shaft 214 and a pin hole 218 on the adapter 212, or otherwise). As described below with reference to FIGS. 4A to 5F, the articulating torque transmission unit 210 is configured to transmit rotation of the shaft 208 and/or torque to the driver head adapter 212.

Figure 3D:
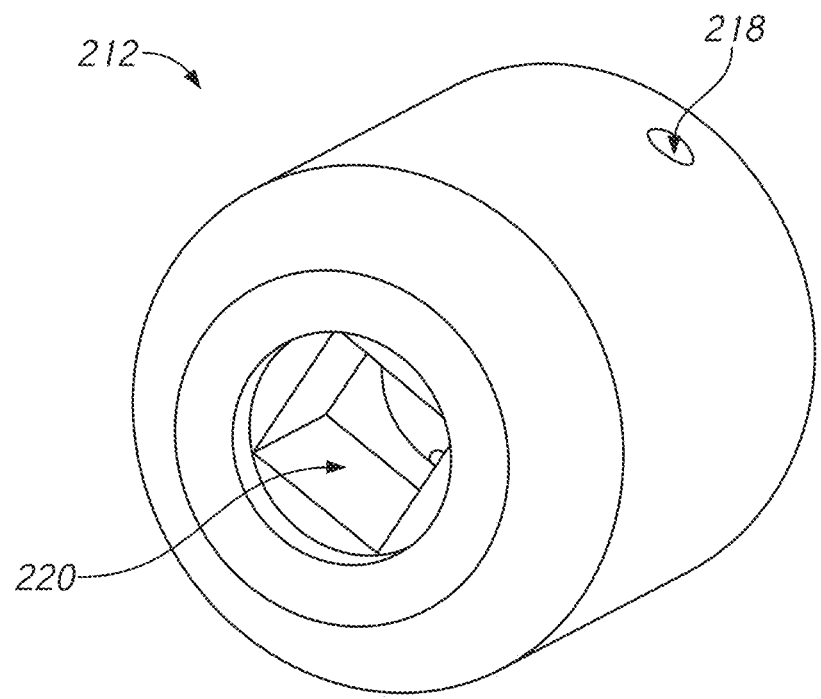
FIG. 3D illustrates a perspective view of an example driver head adapter of the fastening tool of FIG. 3A.
Figure 3E:
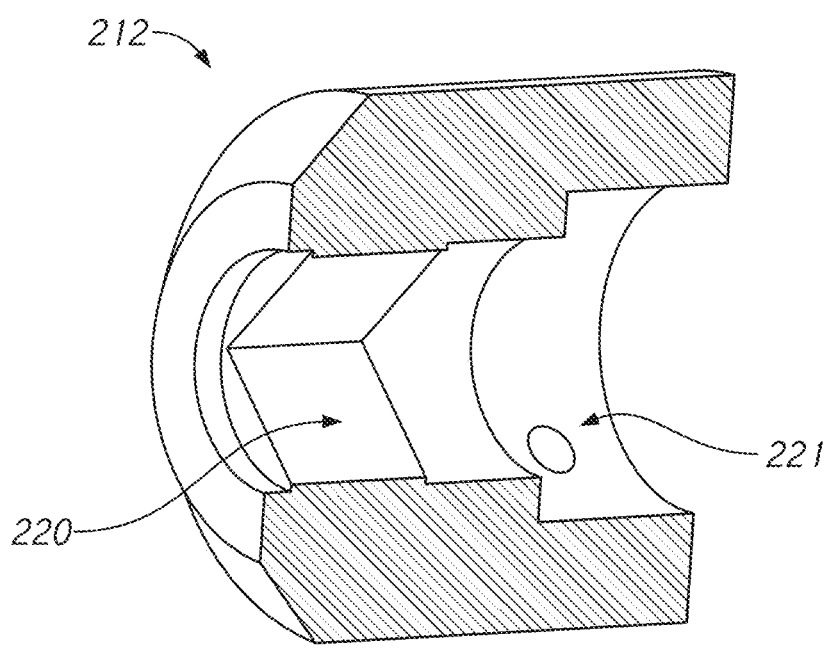
FIG. 3E illustrates a perspective view of the driver head adapter of FIG. 3C sectioned along a central longitudinal axis.

The driver head adapter 212 can be configured to removably receive a driver head 400, such as a bit (e.g., a flat-head bit, Philips bit, hex bit, star bit, or otherwise). In some embodiments, such as shown in FIGS. 3D and 3E, the adapter 212 can include a generally square opening 220 configured to receive a driver head having a shaft with a generally square cross-section. In certain embodiments, the driver head adapter 212 can include an opening of a different shape that is complementary to the shape of the driver head shaft and that causes rotation of the driver head adapter 212 to be transmitted to the driver head shaft. As shown, the driver head adapter 212 can include a second opening 221 that has a greater internal dimension than the square opening 220.

Figure 3F:
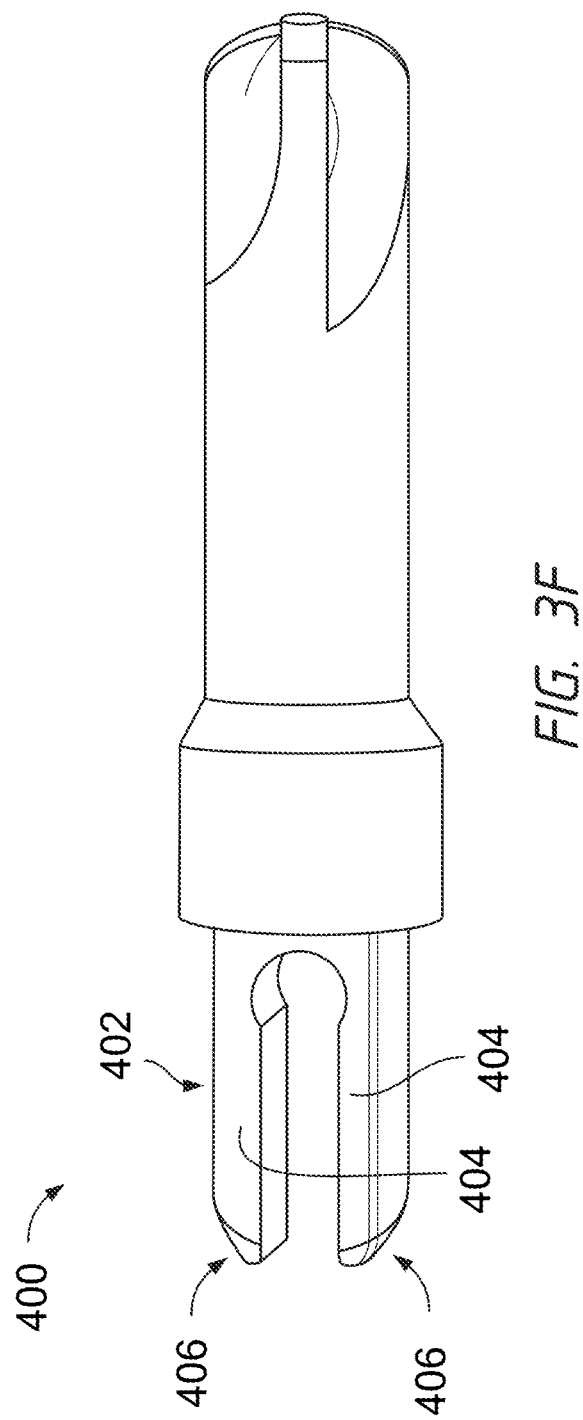
FIG. 3F illustrates a perspective view of an example driver head.

In various embodiments, a driver head shaft 402 can be retained in the adapter 212. For example, the driver head shaft 402 can be retained with a friction fit, detent mechanism, or otherwise. In some implementations, such as shown in FIG. 3F, the driver head shaft 402 of the driver head 400 can include two or more opposing prongs 404 separated by a gap such that a distance between outer surfaces of the prongs 404 is greater than a width of the generally square opening 220. The prongs 404 can deflect slightly toward each other when inserted into the generally square opening 220. The tendency of the prongs 404 to spring apart back to the original gap size can aid in retaining the driver head shaft 304 inside the square opening 220. In some embodiments, the prong 404 can have a chamfer or tapering 406 at its free end to facilitate insertion of the prongs 404 into the generally square opening 220. The prongs 404 of the driver head shaft 402 can expand after the driver head shaft 402 advances past the square opening 220 into the second opening 221, which can aid in retaining the driver head shaft 402 within the driver head adapter 212. In some embodiments, the shaft of the driver head can include other types of retaining mechanism(s), such as spring-biased ball detent or others, so that the second opening 221 can retain the driver head shaft when the driver head shaft advances past the square opening 220 into the second opening 221. In various embodiments, the adapter 212 and driver head shaft 402 are spaced apart from the proximal end of the tool 200 and/or the handpiece 10, such as by at least about: 100 mm, 150 mm, 200 mm, 250 mm, or more.

Figure 4A:
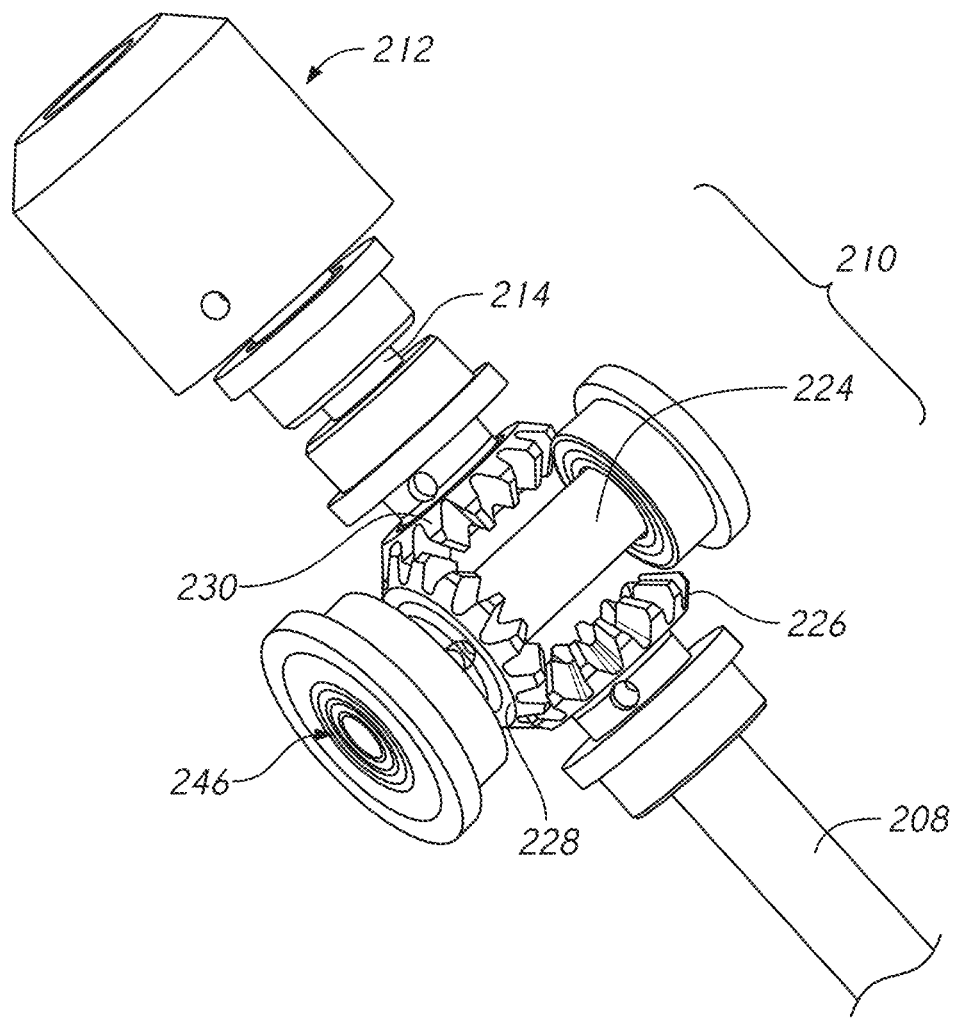
FIG. 4A illustrates a perspective view of an example distal portion of the fastening tool of FIG. 2, with support walls and an outer housing not shown for illustration purposes.

As shown in FIG. 4A, the articulating torque transmission unit 210 can include a first bevel gear 226 fixedly coupled to the first shaft 208, a second bevel gear 228 fixedly coupled to a gear support shaft 224, and third bevel gear 230 fixedly coupled to the output shaft 214. The first bevel gear 226 interacts with the second bevel gear 228. The second bevel gear 228 interacts with the third bevel gear 230. In some embodiments, the bevel gears can include a metal, such as 440C stainless steel or otherwise. In certain embodiments, the gears can have a Rockwell hardness of at least about 60-65 C. As shown in FIGS. 2 and 3A, the articulating torque transmission unit 210 can include one or more support walls 232, which can protect the bevel gears and/or the shafts from external impacts.

Figure 4B:
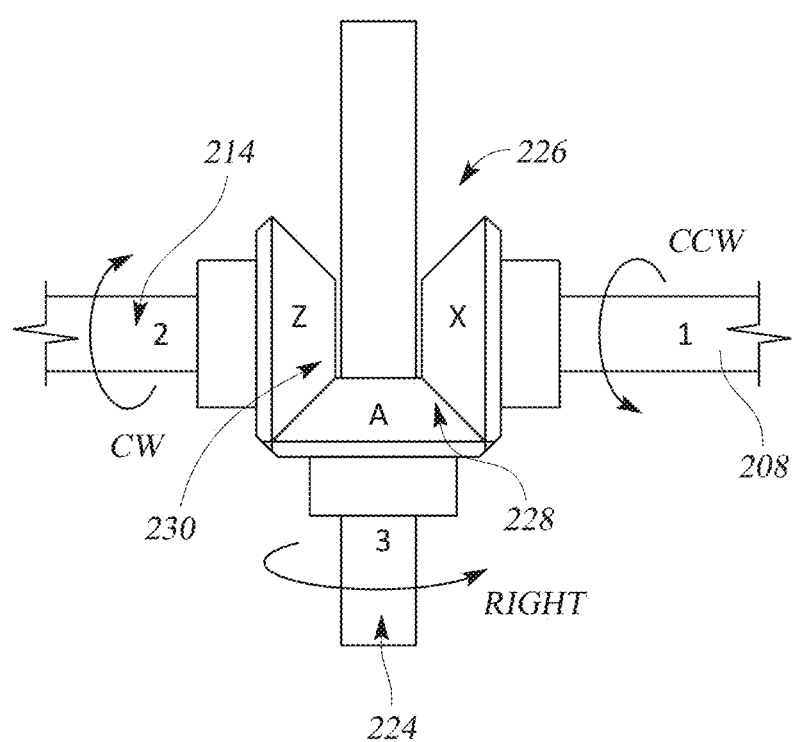
FIG. 4B illustrates operation of an example articulating (e.g., bevel gear) arrangement of the fastening tool of FIG. 4A.

As shown in FIG. 4B, as the first bevel gear 226 and the first shaft 208 rotate in a first direction (e.g., counterclockwise), the second bevel gear 228 and the gear support shaft 224 rotate in a second direction perpendicular to the first direction (e.g., to the right as indicated in the figure). The rotation of the second bevel gear 228 causes the third bevel gear 230 and the output shaft 214 to rotate in a third direction that is opposite the first direction (e.g., clockwise). In various embodiments, an axis of rotation of the second bevel gear 228 is generally perpendicular to an axis of rotation of the first and/or third bevel gear 226, 230. In certain implementations, the axes of rotation of the first and third bevel gears 226, 230 are generally parallel and/or collinear when the driver head is not articulated.

Figure 5A:
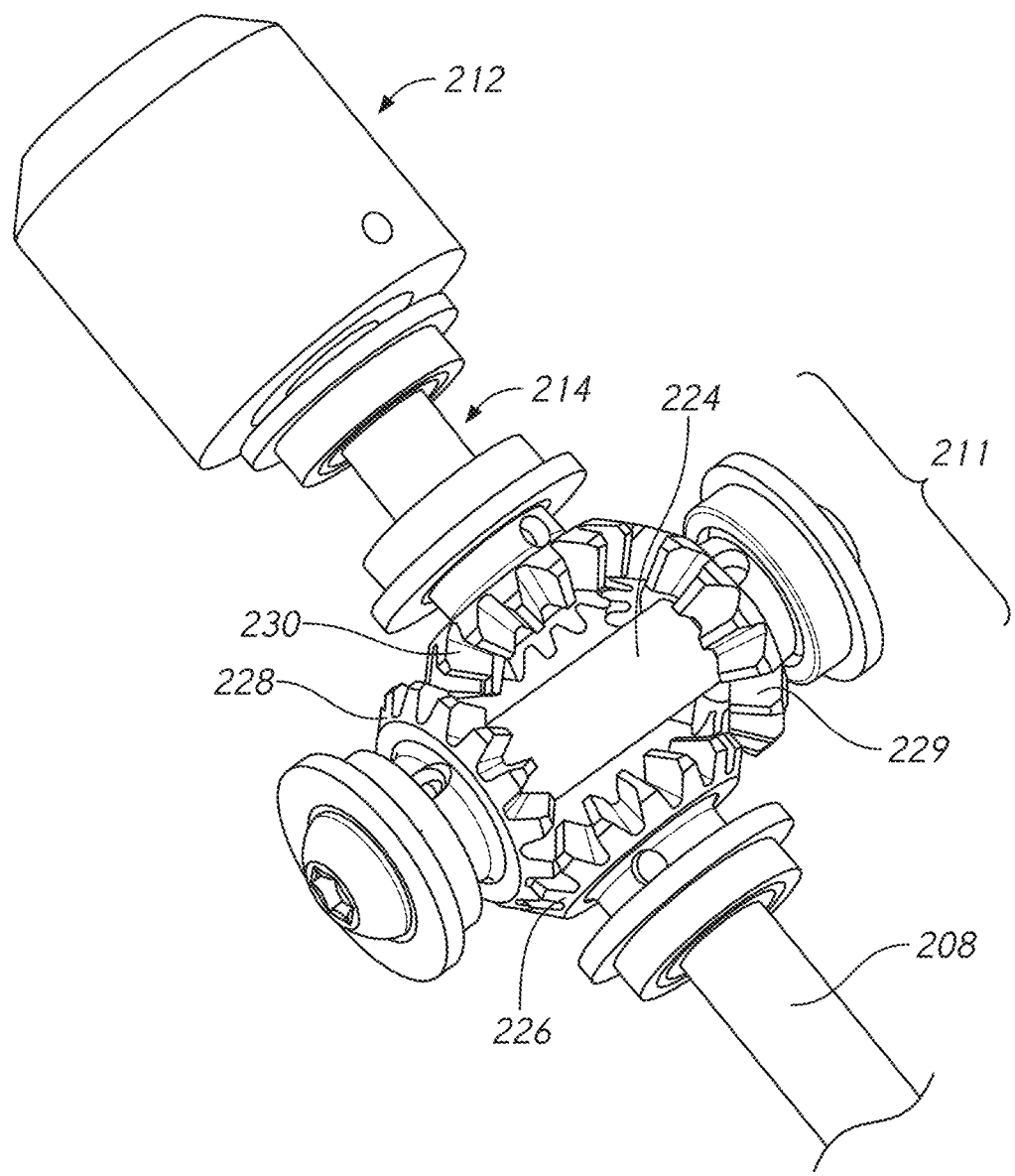
FIG. 5A illustrate a perspective view of another example distal portion of the fastening tool of FIG. 2, with the support walls and outer housing not shown for illustration purposes.

In some embodiments, the fastening tool can include an articulation unit 211 such as shown in FIG. 5A. The articulation unit 211 can include a first bevel gear 226 fixedly coupled to the first shaft 208, a second bevel gear 228 and a third bevel gear 229 fixedly coupled to two ends of a gear support shaft 224, and a fourth bevel gear 230 fixedly coupled to the output shaft 214. The first bevel gear 226 interacts with the second bevel gear 228. Rotation of the second bevel gear 228 is transmitted to the third bevel gear 229 via the gear support shaft 224. The third bevel gear 229 interacts with the fourth bevel gear 230. FIGS. 5B-5E show schematic illustrations of the articulating torque transmission unit 210 with four bevel gears, such as shown in FIG. 5A.

Figure 5B:
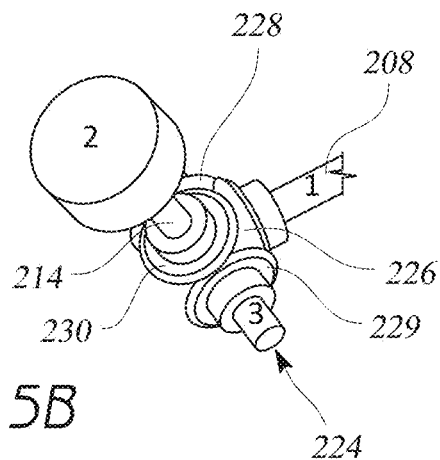
FIGS. 5B-5E illustrate various perspective views of an example bevel gear arrangement in the fastening tool of FIG. 5A.
Figure 5C:
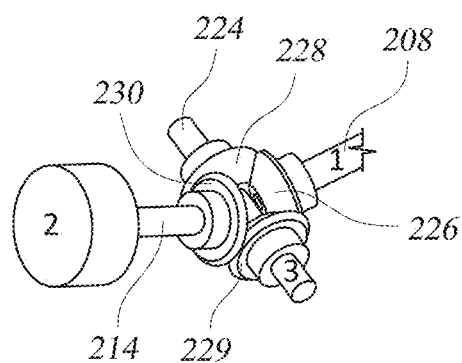
Figure 5D:
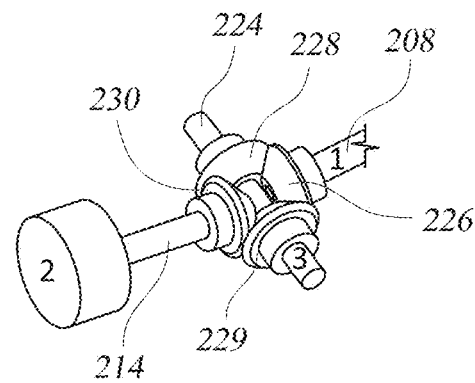
Figure 5E:
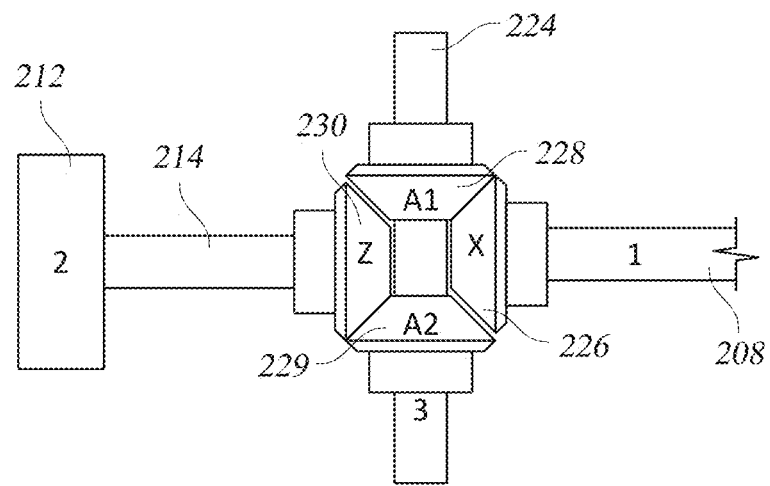
Figure 5F:
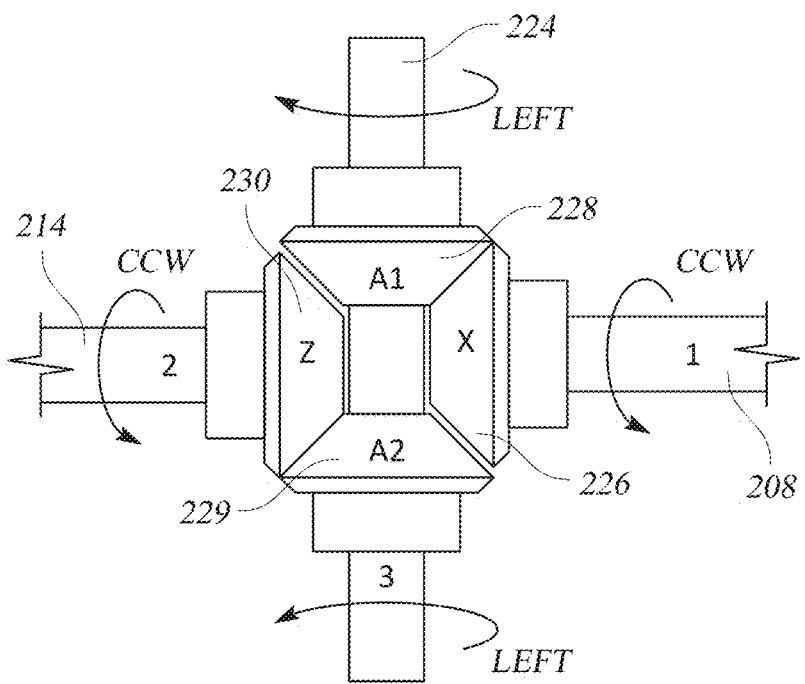
FIG. 5F illustrates operation of the bevel gear arrangement of FIG. 5A.

In some embodiments, such as shown in FIG. 5F, as the first bevel gear 226 and the first shaft 208 rotate in a first direction (e.g., counterclockwise), the second bevel gear 228, the gear support shaft 224, and the third bevel gear 229 rotate in a second direction perpendicular to the first direction (e.g., to the left). The rotation of the third bevel gear 229 causes the fourth bevel gear 230 and the output shaft 214 to rotate in the same direction as the first direction (e.g., counterclockwise).

The articulating torque transmission unit 210 in FIGS. 4A-4B and 5A-5F can allow for improved ranges of motion, such as between the first gear 226 and the third gear 230 in the embodiment shown in FIGS. 4A-4B and between the first gear 226 and the fourth gear 230 in the embodiment shown in FIGS. 5B-5D. An embodiment of the articulating torque transmission unit 210 with four bevel gears, such as shown in FIGS. 5A-5F, can advantageously allow the rotation of the output shaft 224 to be in the same direction as the first shaft 208. For example, input rotation in a direction from the handpiece 10 can result in output rotation in the same direction at the driver head 400.

An embodiment of the articulating torque transmission unit 210 with three bevel gears, such as shown in FIGS. 4A-4B, can result in the rotation of the output shaft 224 being reversed relative to the rotation of the first shaft 208. Having the output shaft 224 rotate in the opposite direction from the first shaft 208 may be confusing to a user. For example, a user may become familiar with a certain button that causes the articulating tool 1 to output clockwise rotation, so the user may be confused when, after the tool 200 is connected, the articulating tool 1 outputs counterclockwise rotation. Some embodiments are configured to automatically adapt to accommodate for the rotation reversal. For example, the handpiece 10 can reverse the drive direction of the motor for the button in response to the tool 200 being connected to the handpiece 10. In some variants, the button drives the handpiece drive shaft in a first direction (e.g., clockwise) before the tool 200 is connected to the handpiece 10 and, after the tool 200 is connected to the handpiece 10, the button drives the handpiece drive shaft in a second direction (e.g., counterclockwise), which in turn causes the driver head 300 to rotate in the first direction (e.g., clockwise). The reversal can be performed through software on a controller of the handpiece 10. The reversal can occur automatically in response to connection of the tool 200 and/or can be invisible to the user.

Various embodiments include an articulation mechanism. In some embodiments, such as shown in FIG. 6A, the articulation mechanism includes a second shaft 234. The shaft 234 can be positioned inside and/or extend through the lumen of the elongate outer housing 202. The second shaft 234 can run generally parallel to the first shaft 208. A proximal portion of the second shaft 234 can include a rotation limitation feature 236 (e.g., one or more flat surfaces). The proximal portion of the second shaft 234 can extend through an opening of a stopper 238 that is located distally from and near a distal end of the collet housing 302. The opening of the stopper 238 that engages the proximal portion of the second shaft 234 can have a shape generally complementary to the rotation limitation feature 236. The stopper 238 can be fixedly attached to the distal end of the collet housing 302 such as the second shaft 234 is prevented substantially from rotational movements.

In some embodiments, at least part of the proximal portion of the second shaft 234 can include helical threads (e.g., external threads). An actuator (such as a wheel 240, a worm gear, or otherwise) can include corresponding helical threads (e.g., internal threads or external threads) that engage the threads on the second shaft 234. As the second shaft 234 is substantially prevented from rotational movements due to the engagement between the rotation limitation feature 236 and the stopper 238, rotating the wheel 240 can cause axial movements of the second shaft 234. Rotating the wheel 240 in one direction can cause the second shaft 234 to advance distally toward the driver head adapter 212. Rotating the wheel 240 in the opposite direction can cause the second shaft 234 to retract proximally away from the driver head adapter 212.

Figure 6B:
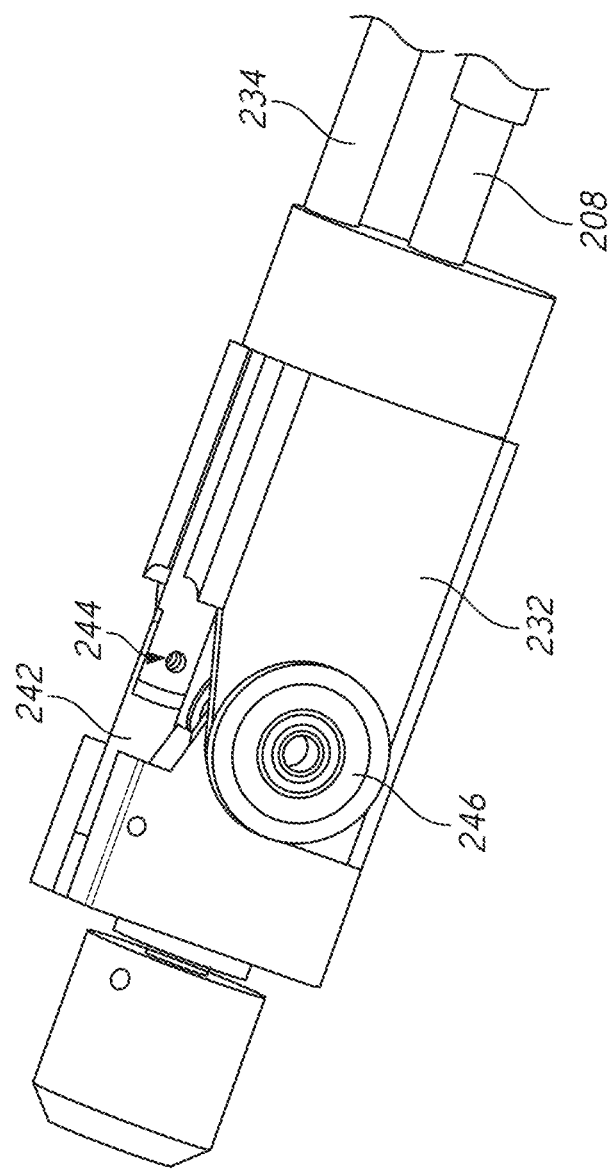
FIG. 6B illustrates a detailed view of the distal portion of the fastening tool of FIG. 6A.

A distal portion of the second shaft 234 can extend distally from the elongate outer housing 202 and into the articulating torque transmission unit 210. A linkage arm 242 can be coupled to a distal end of the second shaft 234 at a hinge 244. As shown in FIGS. 6A and 6B, the support walls 232 of the articulating torque transmission unit 210 can include a gap configured to slidably engage the second shaft 234 and the linkage arm 242. An end of the linkage arm 242 that is opposite the end coupled to the hinge 244 can be pivotally coupled to the support walls 232 (e.g., via a pivot pin extending generally transversely through the support walls and the linkage arm 242).

Figure 7A:
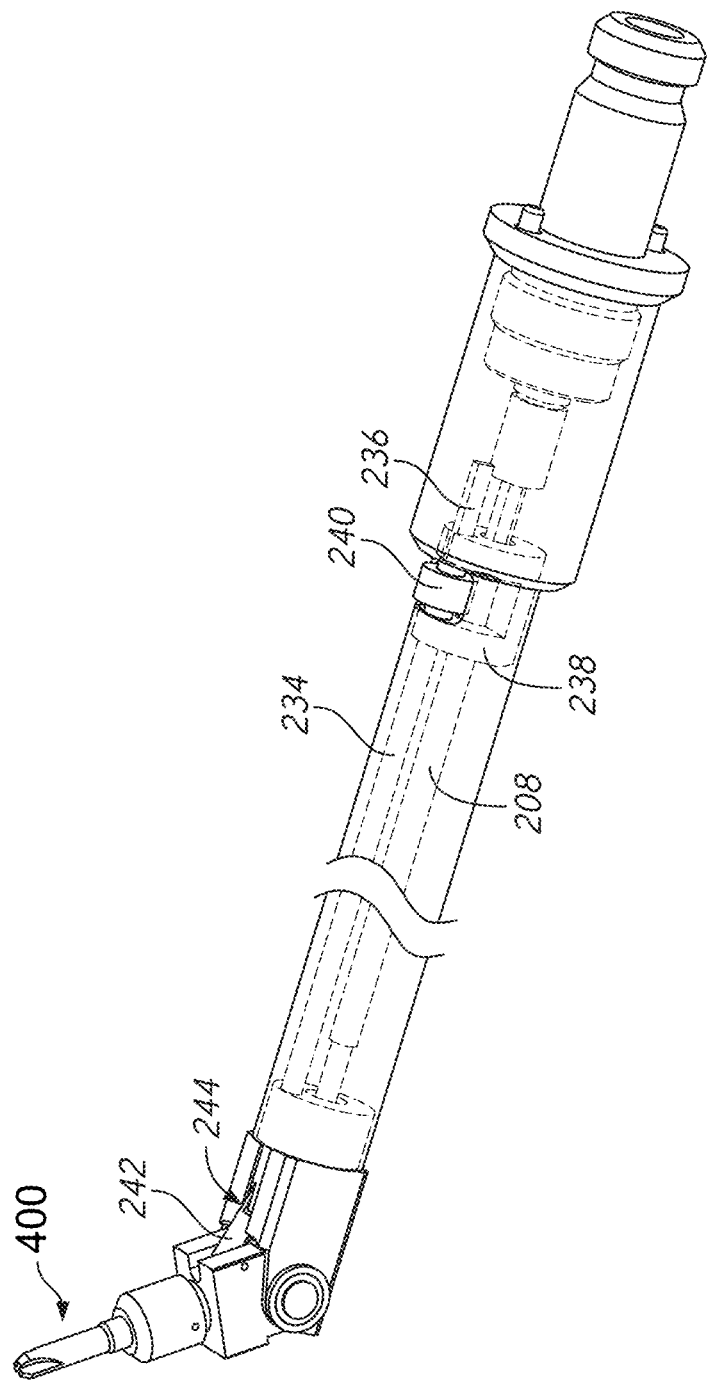
FIG. 7A illustrates a perspective view of the fastening tool of FIG. 2 coupled to an articulating driver head at an acute angle with respect to a longitudinal axis of the fastening tool.
Figure 7B:
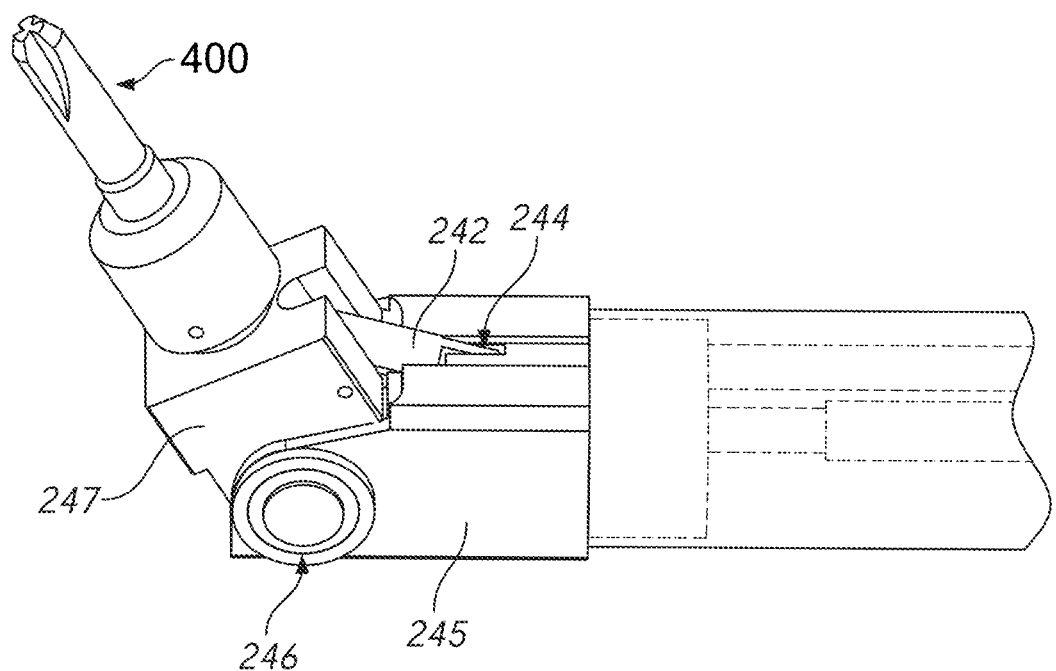
FIG. 7B illustrates a detailed view of the distal portion of the fastening tool of FIG. 7A.

As shown in FIGS. 7A and 7B, the adapter 212 and/or the driver head 300 can be articulated relative to the housing 202. In some implementations, the articulation occurs as a result of movement of the second shaft 234, such due to rotation of the wheel 240 and the threaded engagement of the wheel 240 and the second shaft 234. As shown, proximal movement of the second shaft 234 (e.g., relative to housing 202 and/or wheel 240) can cause the linkage arm 242 to bend at the hinge 244 and rotate relative to the second shaft 234. The support walls 232 can include proximal and distal portions 245, 247 pivotally coupled at a second hinge 246, which is coupled to the gear support shaft 224. The distal portion 247 can be fixedly coupled to the output shaft 214. The bending of the linkage arm 242 can cause the distal portion 247, the driver head adapter 212 (and the driver head 300 coupled to the adapter 212) to pivotally rotate about the second hinge 246 and/or the gear support shaft 224. To straighten the linkage arm 242 relative to the second shaft 234, such as shown in FIG. 6A, the second shaft 234 can be moved distally, for example, by rotating the wheel 240 in the opposite direction.

In various embodiments, the tool 200 can transmit rotation to the driver head 300 while also being able to articulate, such as about the hinge 246. The tool 200 can advantageously drive screws or other fasteners in a variety of positions. The tool 200 can adjust (e.g., bend or pivot) so as to access tight spaces and/or provide a desired orientation of placing and driving the fastener. In various embodiments the mechanism that controls the articulation of the tool is separate (e.g., independently operable) from the mechanism that transmits torque to drive the screws or other fasteners. In some variants, the mechanism that controls the articulation and the mechanism that transmits torque to the driver head can each include a distinct shaft and/or a distinct control device (e.g., actuator). For example, the mechanism that controls the articulation can include the second shaft 234 and/or the wheel 240, and the mechanism that transmits torque to the driver head can include the first shaft 208 and/or one or more buttons on the handpiece 10.

Other Embodiments of an Articulating Fastening Tool

Any of features of the embodiments described below can be incorporated into the fastening tool 200 described above.

Figure 8:
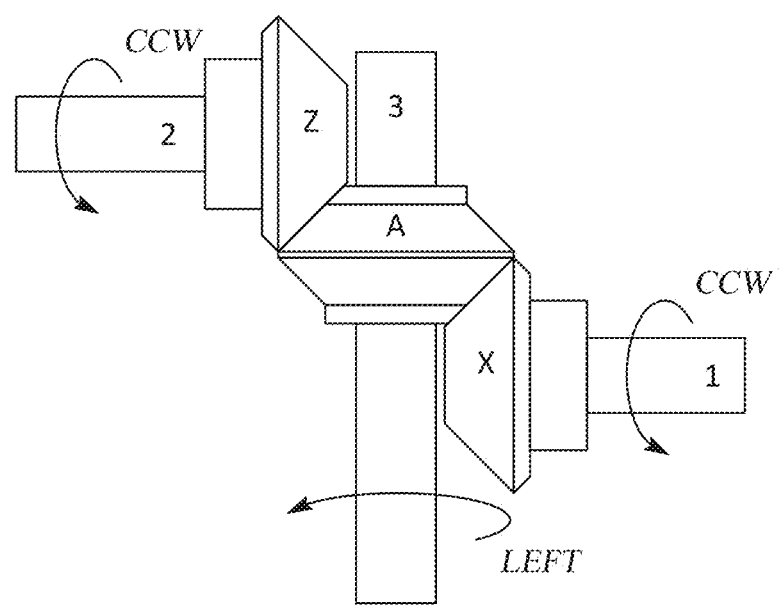
FIG. 8 illustrates operation of another example articulating arrangement.

In some embodiments, such as shown in FIG. 8, the Input Shaft (1) is rigidly connected to Gear 'X'; the Idler Shaft (3) is rigidly connected to Gear 'A' (Gear 'A' is a double sided Bevel Gear); and the Output Shaft (2) is rigidly connected to Gear 'Z'. Gear 'X' interfaces with Gear 'A'. Gear 'A' also interfaces with Gear 'Z'. As Gear 'X' rotates CCW, Gear 'A' rotates to the Left, which causes Gear 'Z' to rotate CCW. An advantage of this arrangement is the increased articulation that can be achieved.

Figure 9:
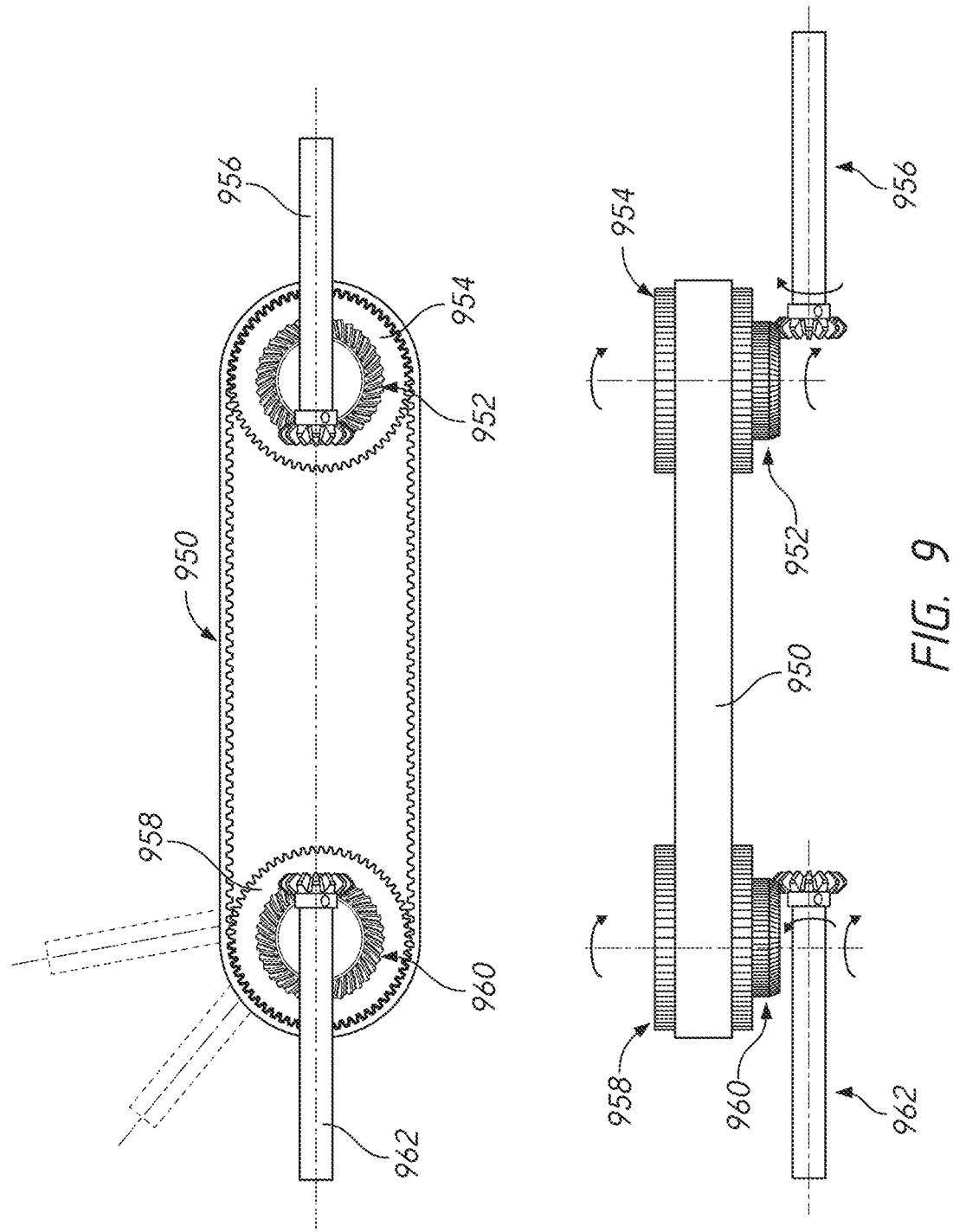
FIG. 9 illustrates operation of another example articulating arrangement.
Figure 10D:
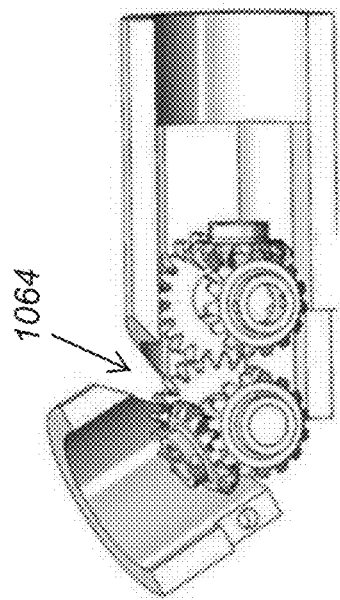
FIG. 10D illustrates a top view of another articulating arrangement.
Figure 10A:
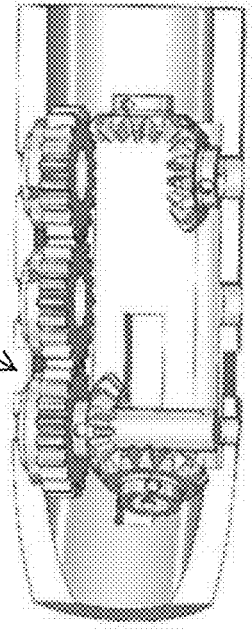
FIG. 10A illustrates a top view of an example articulating gear arrangement with a head substantially not tilted.
Figure 10B:
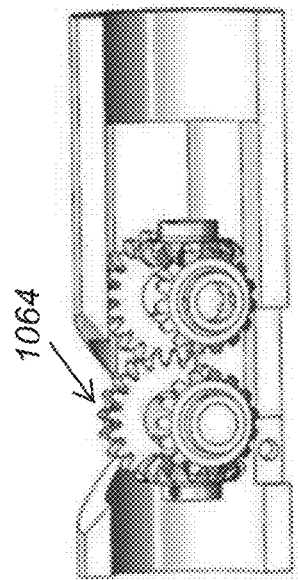
FIG. 10B illustrates a side view of the articulating arrangement of FIG. 10A with a head tilted to a first angle.
Figure 10E:
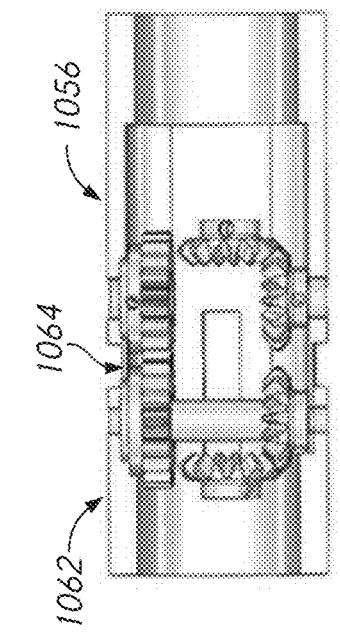
FIG. 10E illustrates a side view of the articulating arrangement of FIG. 10C.
Figure 10C:
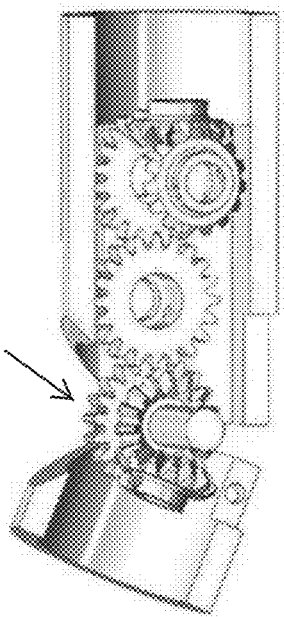
FIG. 10C illustrates a top view of the articulating arrangement of FIG. 10A with the head tilted to a second angle.

Some embodiments are configured to articulate the driver head adapter, (such as past about 45° or about 90°, without the bevel gears directly with one another. In some embodiments, such as shown in FIG. 9, a articulation unit of an articulating fastening tool can include a chain or belt 950. The belt 950 can extend the point from with the motion is transferred from one set of bevel gears to the set of bevel gears. An input shaft 956 can act on a set of bevel gears 952, one of which can be rigidly connected to a belt pulley or chain cog 954. The belt 950 can be connected to a second belt pulley or chain cog 958, which can be connected to a second set of bevel gears 960, one of which acts on an output shaft 962. An advantage of this design is the motion transfer between the input and output bevel gears 952, 960 is effectively repositioned so that the articulating bevel gear will not interfere with the other gearing.

In some embodiments, such as shown in FIGS. 10A-10E, the addition of spur gears 1064 can transfer the motion of the input shaft 1056 to the articulating output shaft 1062. This has a similar effect to the belt and/or chain system discussed above, but does so using additional gears to move the bevel gears into a more effective location. Multiple gears (e.g., two, three, or more) can be added to further displace (e.g., space apart) the bevel gears, if needed. An advantage of this design is the motion transfer between the input and output bevel gears can be repositioned so that the articulating bevel gear does not interfere with the other gearing.

Figure 11:
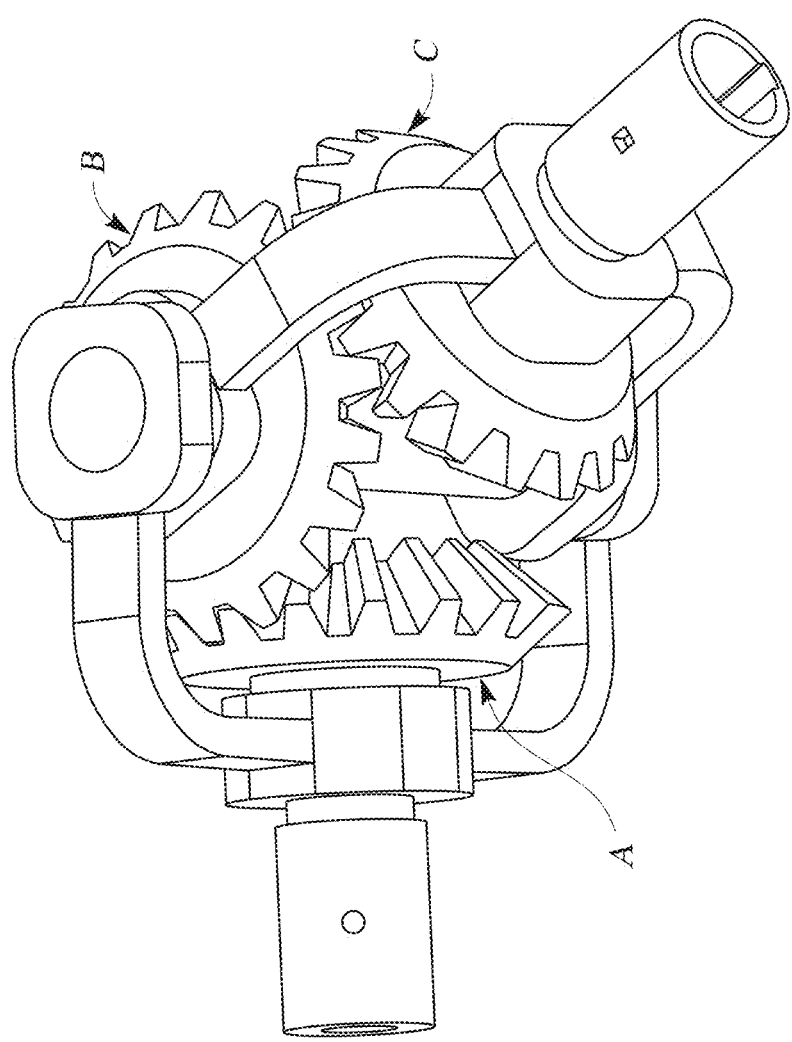
FIG. 11 illustrates a perspective view of another example articulating arrangement.

In some embodiments, the fastening tool can include bevel gears such as shown in FIG. 11. Gear A can be coupled to the drive shaft. Rotation of Gear A gets transferred, via Idler Gear B, to Gear C, which can be coupled to the output shaft to drive the screws. At the same time, Gear C is free to re-orient in 3 dimensions. Some implementations can include a gear reduction or speed multiplication through the idler gear.

Figure 12:
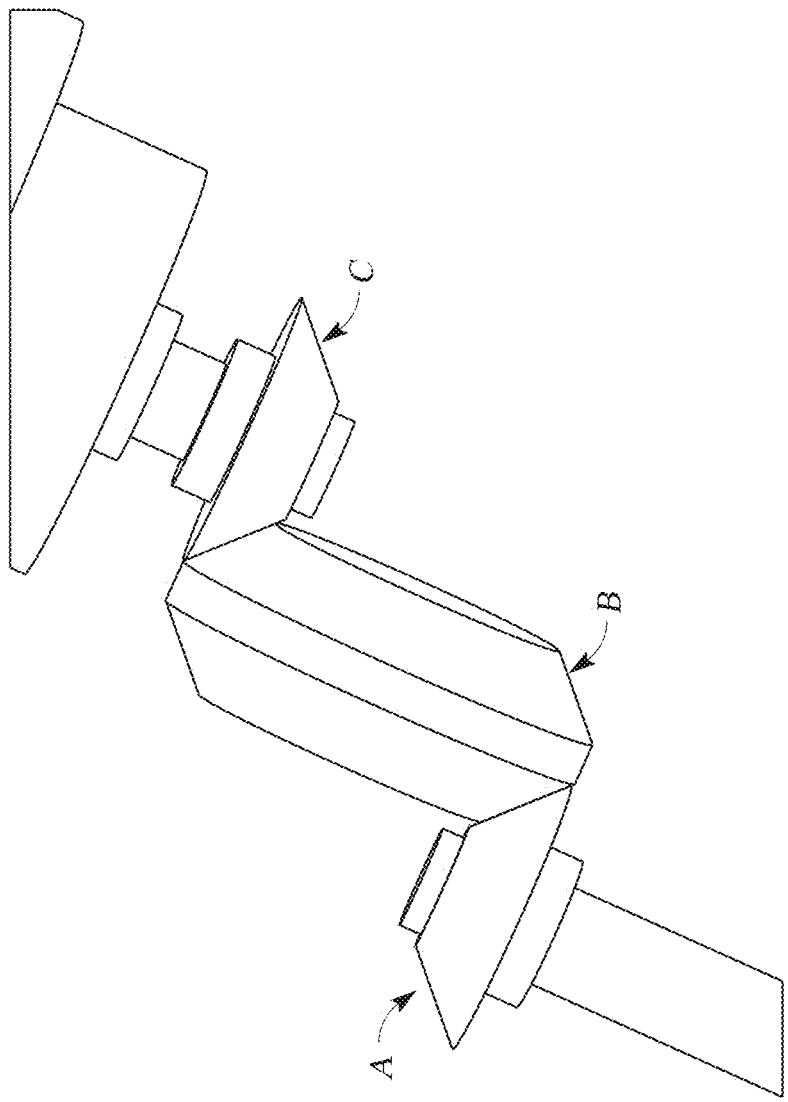
FIG. 12 illustrates a side view of another example articulating arrangement.

In some embodiments, such as shown in FIG. 12, other configurations of bevel gears can transfer the rotation through the articulating joint. In the configuration shown in FIG. 11, Gear A can constrain (e.g., due to a physical interference) the rotation of Gear C. In contrast, in the bevel gear mechanism such as shown in FIG. 12, Gears A and B are arranged symmetrically about the Idler Gear B. As the planes of articulation no longer intersect, the mechanism in FIG. 12 can allow for an increased range of motion compared to, for example, the mechanism in FIG. 11.

Figure 13:
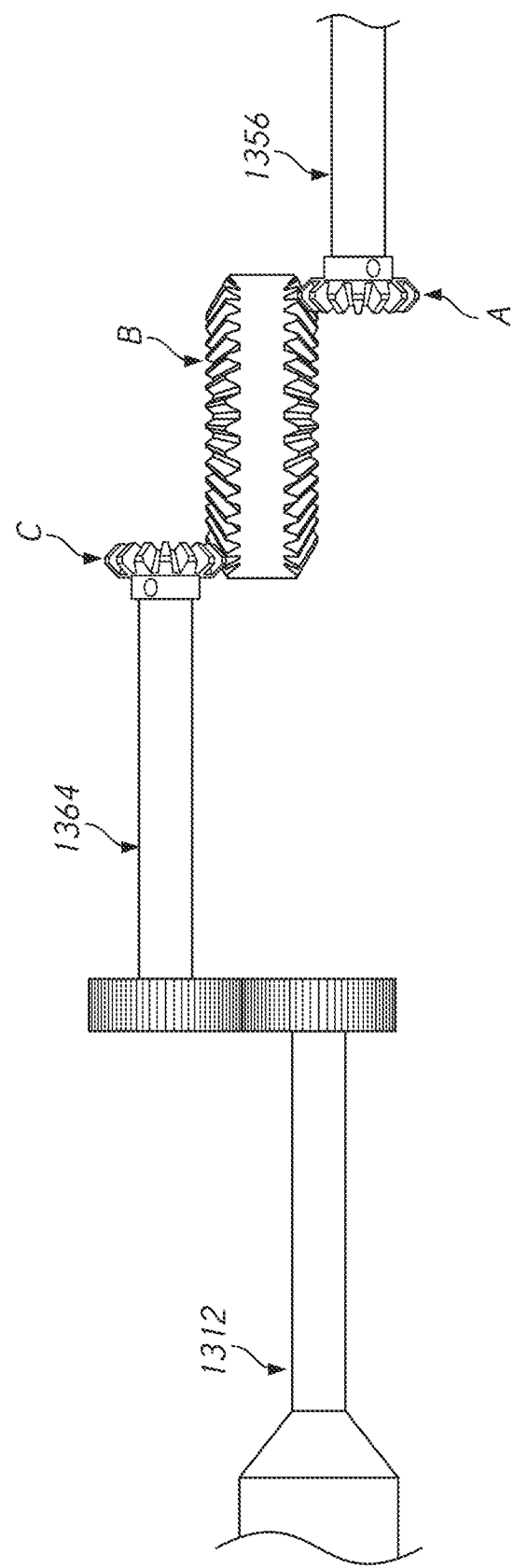
FIG. 13 illustrates another example articulating arrangement.

In some embodiments, such as shown in FIG. 13, the tip of the driver head adapter can be substantially collinear with the drive axis of an input shaft 1356. The bevel gear mechanism in FIG. 12 introduces an offset. Certain embodiments, such as shown in FIG. 13, the gear mechanism of FIG. 12 can be connected to a spur gear 1364 to adjust the offset. As shown, tip of the driver head adapter 1312 can be substantially collinear with the tip of the input shaft 1356.

Figure 14:
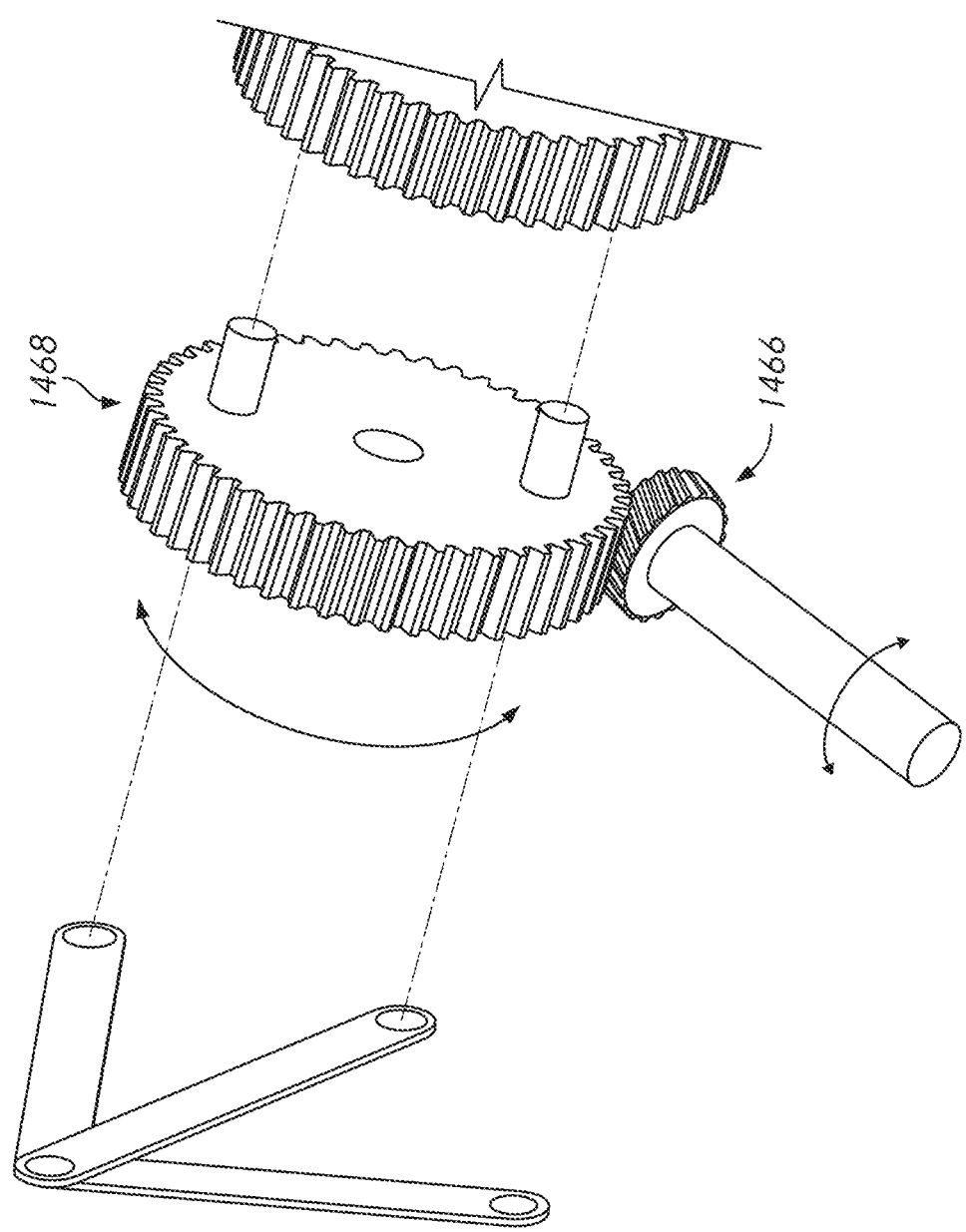
FIG. 14 illustrates an example worm gear arrangement.

Various embodiments of an articulating fastening tool can be configured to control the orientation of the driver head adapter 212 at a location away from the driver head adapter 212 and/or closer to the handpiece 10. Some embodiments, such as shown in FIG. 14, can include a worm gear 1466 acting on a gear or adapter adjustment dial 1468. The adjustment dial 1468 can serve as a user interface (e.g., located near a proximal end of the fastening tool or on the handpiece). Rotating the adjustment dial 1468 can articulate (e.g., open or close) the mechanical linkage on the left side of the adjustment dial 1468 (e.g., from about 0° to about) 90°. In certain embodiments, the linkage can translate rotational motion about the shaft axis to an axis generally perpendicular to the shaft axis and about which the driver head can rotate or articulate. In some variants, rotation of the adapter adjust dial 1468 can rotate the worm gear 1466 and the driver head adapter accordingly.

Figure 15:
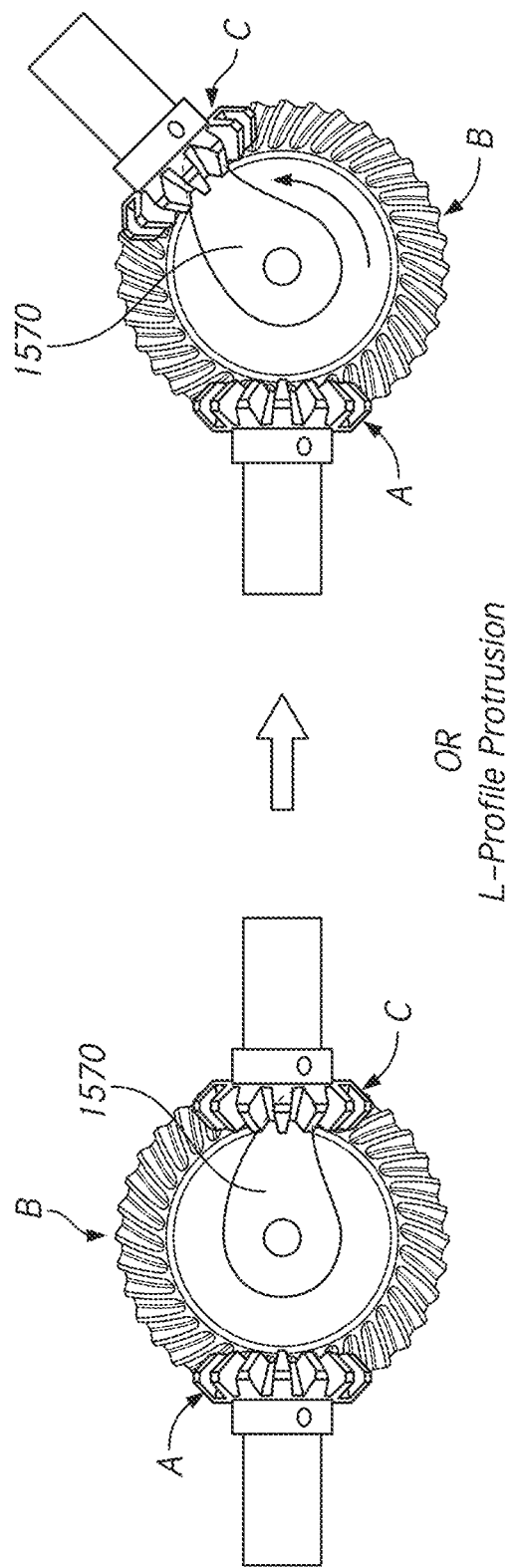
FIG. 15 illustrates an example cam and/or pin articulating arrangement.

Some embodiments can have a stationary cam or pin 1570 such as shown in FIG. 15, for articulating the driver head adapter and/or the driver head. Gear B and the cam or pin 1570 are mounted to the same shaft or axis, but are free to rotate independently of one another. The cam or pin 1570 is connected to the shaft, while Gear B has a bearing that allows Gear B to rotate independently of the shaft. The center of Gear C is fixed to the end of the cam or pin 1570. The cam or pin 1570 can protrude into the moveable output bevel gear (such as Gear C described above), but does not rotate with respect to the rotation of the moveable output bevel gear. When the cam or pin 1570 is rotated about the connected shaft, Gear C can rotate with the cam or pin 1570 along the surface of Gear B. However, the cam or pin 1570 is fixed to the center of Gear C such that Gear C is free to spin about the center axis of the shaft. The cam or pin 1570 can be actuated via a rod sliding back and forth similar to the rod 1674 in FIG. 16. A gear similar to the gear 1678 but smaller in size can connect to the shaft to which the cam or pin 1570 is mounted to.

Figure 16:
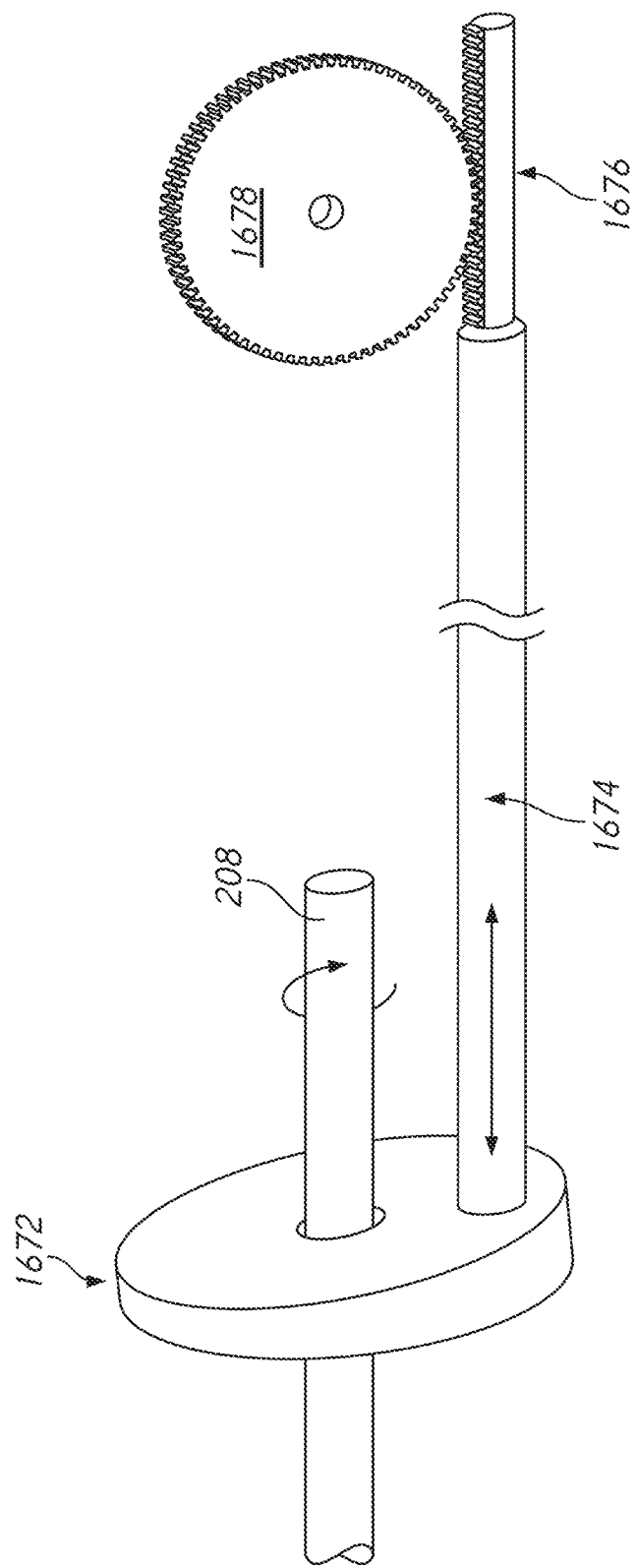
FIG. 16 illustrates an example swash plate or angled plate articulating arrangement.

Certain implementations can use mechanical linkages that are activated by a rod that pushes and pulls on the adapter, for example, such as shown in FIG. 16. The rod can be activated by advancing the adjustment dial on a threaded track. Some embodiments, such as shown in FIG. 16, can have a swash plate 1672 (or angled plate). The swash plate 1672 can be angled relative to the longitudinal axis of the tool 200. The swash plate 1672 can be configured to abut against and/or articulate the driver head adapter 212 and/or the driver head 300. In some embodiments, the swash plate 1672 acts against a push rod 1674. For example, the swash plate 1672 can rotate relative to the push rod 1674, which due to the angle of the swash plate 1672, causes the push rod 1674 to move longitudinally. In implementations, the push rod 1674 translates a rack gear 1676, which activates a gear 1678 that is used to control the orientation of the driver head adapter 212 and/or the driver head 300. In some embodiments, the shaft 208 extends through the swash plate 1672 and/or can rotate relative to the swash plate 1672.

Several embodiments of the fastening tool can enable the input shaft to be rotated 360°. In some embodiments, the 360° rotation of the input shaft is achieved by retracting the pins allowing for discrete rotation of the driver head adapter with respect to the driver unit. In some embodiments, rotation of the input shaft is achieved with a friction fit between the input shaft and the body interface (e.g., the housing 202) so that the input shaft can be manually rotated to the desired orientation. In some embodiments, such as shown in FIG. 17, the 360° rotation of the input shaft 1756 can be achieved by utilizing a gear type system by which an adjustment dial 1770 (e.g., in a direction perpendicular to the rotation of the input shaft 1756) can be used to rotate a gear 1772. The gear 1772 can control the orientation of the shaft 1756 with respect to the driver unit. In the embodiments such as shown in FIG. 17, the driver head can stay fixed to the fastening tool as the gear 1772 is rotated to rotate the driver head.

Certain Terminology

Terms of orientation used herein, such as "top," "bottom," "horizontal," "vertical," "longitudinal," "lateral," and "end" are used in the context of the illustrated embodiment. However, the present disclosure should not be limited to the illustrated orientation. Indeed, other orientations are possible and are within the scope of this disclosure. Terms relating to circular shapes as used herein, such as diameter or radius, should be understood not to require perfect circular structures, but rather should be applied to any suitable structure with a cross-sectional region that can be measured from side-to-side. Terms relating to shapes generally, such as "circular" or "cylindrical" or "semi-circular" or "semi-cylindrical" or any related or similar terms, are not required to conform strictly to the mathematical definitions of circles or cylinders or other structures, but can encompass structures that are reasonably close approximations.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

The terms "approximately," "about," and "substantially" as used herein represent an amount close to the stated amount that still performs a desired function or achieves a desired result. For example, in some embodiments, as the context may permit, the terms "approximately", "about", and "substantially" may refer to an amount that is within less than or equal to 10% of the stated amount. The term "generally" as used herein represents a value, amount, or characteristic that predominantly includes or tends toward a particular value, amount, or characteristic. As an example, in certain embodiments, as the context may permit, the term "generally parallel" can refer to something that departs from exactly parallel by less than or equal to 15 degrees. As another example, in certain embodiments, as the context may permit, the term "generally perpendicular" can refer to something that departs from exactly perpendicular by less than or equal to 15 degrees.

CONCLUSION

While a number of variations of the disclosure have been shown and described in detail, other modifications, which are within the scope of this disclosure, will be readily apparent to those of skill in the art based upon this disclosure. For example, although several embodiments are discussed above with bevel gears, other types of gears (e.g., spur gears, spline gears, spiral bevel gears, miter gears, helical gears, etc.) and other torque transmission devices are contemplated. It is also contemplated that various combinations or sub-combinations of the specific features and aspects of the embodiments may be made and still fall within the scope of the disclosure. Accordingly, it should be understood that various features and aspects of the disclosed embodiments can be combined with or substituted for one another in order to form varying modes of the disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings) may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination so disclosed.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Some embodiments have been described in connection with the accompanying drawings. The figures are drawn to scale where appropriate, but such scale should not be limiting, since dimensions and proportions other than what are shown are contemplated and are within the scope of the disclosed invention. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, any methods described herein may be practiced using any device suitable for performing the recited steps.

Although this invention has been disclosed in the context of certain embodiments and examples, the scope of this disclosure extends beyond the specifically disclosed embodiments to other alternative embodiments and/or uses of the invention and obvious modifications and equivalents thereof. Any system, method, and device described in this application can include any combination of the preceding features described in this and other paragraphs, among other features and combinations described herein, including features and combinations described in subsequent paragraphs. While several variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Various features and aspects of the disclosed embodiments can be combined with, or substituted for, one another in order to form varying modes of the disclosed invention. Thus, it is intended that the scope of the present invention herein disclosed should not be limited by the particular disclosed embodiments described above, but should be determined only by a fair reading of the claims that follow.

The following is claimed:

1. An offset tool for use with a drive mechanism during a surgical procedure, the offset tool comprising:
    an elongate outer housing comprising a lumen and a longitudinal axis, wherein the elongate outer housing is configured to rotate around the longitudinal axis;
    an offset torque transmission mechanism connected to the elongate outer housing, the offset torque transmission mechanism comprising:
        a first shaft within the lumen of the elongate outer housing;
        an articulating torque transmission unit having:
            a first end that is coupled to a distal portion of the first shaft; and
            a second end that is not collinear with the first end and that comprises a driver head adapter, the driver head adapter configured to removably engage with a bit and to rotate the bit around a bit axis;
        wherein the offset torque transmission mechanism is configured to transmit torque from the drive mechanism to the driver head adapter and the bit; and
    an orientation mechanism that is separate from the offset torque transmission mechanism, the orientation mechanism comprising:
        a second shaft within the lumen of the elongate outer housing; and
        a controller configured to rotate the second shaft;
        wherein a proximal portion of the second shaft is connected to the controller;
        wherein a distal portion of the second shaft is connected to the driver head adapter; and
        wherein rotation of the second shaft rotates the driver head adapter around a transverse axis that is generally perpendicular to the longitudinal axis.

2. The offset tool of claim 1, wherein the articulating torque transmission unit comprises first, second, and third bevel gears, wherein the first bevel gear is fixedly coupled to the first shaft, the second bevel gear is coupled to a gear support shaft, and the third bevel gear is coupled to the driver head adapter.

3. The offset tool of claim 2, wherein the second bevel gear is between the longitudinal axis and the bit axis.

4. The offset tool of claim 2, wherein the first bevel gear intersects with the second gear and the second gear intersects with the third gear.

5. The offset tool of claim 1, wherein the driver head adapter comprises a lumen configured to receive a shaft of the bit.

6. The offset tool of claim 5, wherein the driver head adapter is coupled to the shaft of the bit via a quick-release mechanism.

7. The offset tool of claim 1, wherein the drive mechanism comprises an electric motor.

8. The offset tool of claim 1, wherein the elongate outer housing is configured to rotate relative to the drive mechanism between about 0° to about 360°.

9. The offset tool of claim 1, wherein the driver head adapter is configured to rotate around the transverse axis between about 0° to about 360°.

10. The offset tool of claim 1, wherein the controller comprises a wheel, wherein rotation of the wheel causes the second shaft to rotate.

* * * * *